United States Patent
Wright et al.

(10) Patent No.: US 8,849,680 B2
(45) Date of Patent: Sep. 30, 2014

(54) DOCUMENTATION THROUGH A REMOTE PRESENCE ROBOT

(75) Inventors: Timothy C. Wright, Santa Barbara, CA (US); Fuji Lai, Goleta, CA (US); Marco Pinter, Santa Barbara, CA (US); Yulun Wang, Goleta, CA (US)

(73) Assignee: InTouch Technologies, Inc., Goleta, CA (US)

( * ) Notice: Subject to any disclaimer, the term of this patent is extended or adjusted under 35 U.S.C. 154(b) by 891 days.

(21) Appl. No.: 12/362,454

(22) Filed: Jan. 29, 2009

(65) Prior Publication Data

US 2010/0191375 A1    Jul. 29, 2010

(51) Int. Cl.
G06F 17/00 (2006.01)
G06F 19/00 (2011.01)
G05B 15/00 (2006.01)
G06Q 30/00 (2012.01)
B25J 9/16 (2006.01)
G06Q 30/02 (2012.01)

(52) U.S. Cl.
CPC ..... *B25J 9/1689* (2013.01); *G05B 2219/45117* (2013.01); *G06Q 30/0283* (2013.01); *G06F 19/3418* (2013.01)
USPC ............... 705/2; 700/264; 700/245

(58) Field of Classification Search
USPC ............................................. 705/2
See application file for complete search history.

(56) References Cited

U.S. PATENT DOCUMENTS

| | | | |
|---|---|---|---|
| 3,821,995 A | 7/1974 | Aghnides | |
| 4,413,693 A | 11/1983 | Derby | |
| 4,471,354 A | 9/1984 | Smith | |
| 4,519,466 A | 5/1985 | Shiraishi | |
| 4,572,594 A | 2/1986 | Schwartz | |
| 4,625,274 A | 11/1986 | Schroeder | |
| 4,638,445 A | 1/1987 | Mattaboni | |
| 4,652,204 A | 3/1987 | Arnett | |
| 4,669,168 A | 6/1987 | Tamura et al. | |
| 4,679,152 A | 7/1987 | Perdue | |
| 4,697,472 A | 10/1987 | Hiyane | |
| 4,709,265 A | 11/1987 | Silverman et al. | |

(Continued)

FOREIGN PATENT DOCUMENTS

| | | |
|---|---|---|
| AU | 1216200 A | 5/2000 |
| CA | 2289697 A1 | 11/1998 |

(Continued)

OTHER PUBLICATIONS

Goldenberg, et al., "Telemedicine in Otolaryngology", American Journal of Otolaryngology, vol. 23, No. 1, 2002, pp. 35-43.

(Continued)

*Primary Examiner* — Hiep V Nguyen
(74) *Attorney, Agent, or Firm* — Chris Lambrecht

(57) ABSTRACT

A robotic system that is used in a tele-presence session. For example, the system can be used by medical personnel to examine, diagnose and prescribe medical treatment in the session. The system includes a robot that has a camera and is controlled by a remote station. The system further includes a storage device that stores session content data regarding the session. The data may include a video/audio taping of the session by the robot. The session content data may also include time stamps that allow a user to determine the times that events occurred during the session. The session content data may be stored on a server that accessible by multiple users. Billing information may be automatically generated using the session content data.

29 Claims, 8 Drawing Sheets

(56) References Cited

U.S. PATENT DOCUMENTS

| | | |
|---|---|---|
| 4,733,737 A | 3/1988 | Falamak |
| 4,751,658 A | 6/1988 | Kadonoff et al. |
| 4,766,581 A | 8/1988 | Korn et al. |
| 4,777,416 A | 10/1988 | George, II et al. |
| 4,797,557 A | 1/1989 | Ohman |
| 4,803,625 A | 2/1989 | Fu et al. |
| 4,847,764 A | 7/1989 | Halvorson |
| 4,875,172 A | 10/1989 | Kanayama |
| 4,878,501 A | 11/1989 | Shue |
| 4,942,512 A | 7/1990 | Kohno |
| 4,942,538 A | 7/1990 | Yuan et al. |
| 4,953,159 A | 8/1990 | Hayden et al. |
| 4,974,607 A | 12/1990 | Miwa |
| 4,977,971 A | 12/1990 | Crane, III et al. |
| 5,006,988 A | 4/1991 | Borenstein et al. |
| 5,040,116 A | 8/1991 | Evans et al. |
| 5,051,906 A | 9/1991 | Evans, Jr. et al. |
| 5,073,749 A | 12/1991 | Kanayama |
| 5,084,828 A | 1/1992 | Kaufman et al. |
| 5,130,794 A | 7/1992 | Ritchey |
| 5,148,591 A | 9/1992 | Pryor |
| 5,153,833 A | 10/1992 | Gordon et al. |
| 5,155,684 A | 10/1992 | Burke et al. |
| 5,157,491 A | 10/1992 | Kassatly |
| 5,182,641 A | 1/1993 | Diner et al. |
| 5,186,270 A | 2/1993 | West |
| 5,193,143 A | 3/1993 | Kaemmerer et al. |
| 5,217,453 A | 6/1993 | Wilk |
| 5,224,157 A | 6/1993 | Yamada et al. |
| 5,230,023 A | 7/1993 | Nakano |
| 5,231,693 A | 7/1993 | Backes et al. |
| 5,236,432 A | 8/1993 | Matsen, II et al. |
| 5,305,427 A | 4/1994 | Nagata |
| 5,315,287 A | 5/1994 | Sol |
| 5,319,611 A | 6/1994 | Korba |
| 5,341,242 A | 8/1994 | Gilboa et al. |
| 5,341,459 A | 8/1994 | Backes |
| 5,341,854 A | 8/1994 | Zezulka et al. |
| 5,347,306 A | 9/1994 | Nitta |
| 5,347,457 A | 9/1994 | Tanaka et al. |
| 5,350,033 A | 9/1994 | Kraft |
| 5,366,896 A | 11/1994 | Margrey et al. |
| 5,374,879 A | 12/1994 | Pin et al. |
| 5,375,195 A | 12/1994 | Johnston |
| 5,413,693 A | 5/1995 | Redepenning |
| 5,417,210 A | 5/1995 | Funda et al. |
| 5,419,008 A | 5/1995 | West |
| 5,436,542 A | 7/1995 | Petelin et al. |
| 5,441,042 A | 8/1995 | Putman |
| 5,441,047 A | 8/1995 | David et al. |
| 5,442,728 A | 8/1995 | Kaufman et al. |
| 5,462,051 A | 10/1995 | Oka et al. |
| 5,486,853 A | 1/1996 | Baxter et al. |
| 5,510,832 A | 4/1996 | Garcia |
| 5,511,147 A | 4/1996 | Abdel-Malek |
| 5,528,289 A | 6/1996 | Cortjens et al. |
| 5,539,741 A | 7/1996 | Barraclough et al. |
| 5,544,649 A | 8/1996 | David et al. |
| 5,550,577 A | 8/1996 | Verbiest et al. |
| 5,553,609 A | 9/1996 | Chen et al. |
| 5,563,998 A | 10/1996 | Yaksich et al. |
| 5,572,229 A | 11/1996 | Fisher |
| 5,572,999 A | 11/1996 | Funda et al. |
| 5,594,859 A | 1/1997 | Palmer et al. |
| 5,600,573 A | 2/1997 | Hendricks et al. |
| 5,630,566 A | 5/1997 | Case |
| 5,636,218 A | 6/1997 | Ishikawa |
| 5,652,849 A | 7/1997 | Conway et al. |
| 5,657,246 A | 8/1997 | Hogan et al. |
| 5,659,779 A | 8/1997 | Laird et al. |
| 5,673,082 A | 9/1997 | Wells et al. |
| 5,675,229 A | 10/1997 | Thorne |
| 5,682,199 A | 10/1997 | Lankford |
| 5,684,695 A | 11/1997 | Bauer |
| 5,701,904 A | 12/1997 | Simmons et al. |
| 5,739,657 A | 4/1998 | Takayama et al. |
| 5,748,629 A | 5/1998 | Caldara et al. |
| 5,749,058 A | 5/1998 | Hashimoto |
| 5,749,362 A | 5/1998 | Funda et al. |
| 5,754,631 A | 5/1998 | Cave |
| 5,758,079 A | 5/1998 | Ludwig et al. |
| 5,762,458 A | 6/1998 | Wang et al. |
| 5,764,731 A | 6/1998 | Yablon |
| 5,767,897 A | 6/1998 | Howell |
| 5,786,846 A | 7/1998 | Hiroaki |
| 5,787,545 A | 8/1998 | Colens |
| 5,802,494 A | 9/1998 | Kuno |
| 5,836,872 A | 11/1998 | Kenet et al. |
| 5,838,575 A | 11/1998 | Lion |
| 5,857,534 A | 1/1999 | DeVault et al. |
| 5,867,653 A | 2/1999 | Aras et al. |
| 5,871,451 A | 2/1999 | Unger et al. |
| 5,876,325 A | 3/1999 | Mizuno et al. |
| 5,911,036 A | 6/1999 | Wright et al. |
| 5,917,958 A | 6/1999 | Nunally et al. |
| 5,927,423 A | 7/1999 | Wada et al. |
| 5,949,758 A | 9/1999 | Kober |
| 5,954,692 A | 9/1999 | Smith et al. |
| 5,959,423 A | 9/1999 | Nakanishi et al. |
| 5,961,446 A | 10/1999 | Beller et al. |
| 5,966,130 A | 10/1999 | Benman, Jr. |
| 5,973,724 A | 10/1999 | Riddle |
| 5,974,446 A | 10/1999 | Sonnenreich et al. |
| 5,983,263 A | 11/1999 | Rothrock et al. |
| 5,995,119 A | 11/1999 | Cosatto et al. |
| 5,995,884 A | 11/1999 | Allen et al. |
| 5,999,977 A | 12/1999 | Riddle |
| 6,006,946 A | 12/1999 | Williams et al. |
| 6,031,845 A | 2/2000 | Walding |
| 6,036,812 A | 3/2000 | Williams et al. |
| 6,047,259 A | 4/2000 | Campbell et al. |
| 6,113,343 A | 9/2000 | Goldenberg et al. |
| 6,133,944 A | 10/2000 | Braun et al. |
| 6,135,228 A | 10/2000 | Asada et al. |
| 6,148,100 A | 11/2000 | Anderson et al. |
| 6,160,582 A | 12/2000 | Hill |
| 6,170,929 B1 | 1/2001 | Wilson et al. |
| 6,175,779 B1 | 1/2001 | Barrett |
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba et al. |
| 6,233,504 B1 | 5/2001 | Das et al. |
| 6,233,735 B1 | 5/2001 | Ebihara |
| 6,250,928 B1 | 6/2001 | Poggio et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,304,050 B1 | 10/2001 | Skaar et al. |
| 6,317,652 B1 | 11/2001 | Osada |
| 6,321,137 B1 | 11/2001 | De Smet |
| 6,324,184 B1 | 11/2001 | Hou et al. |
| 6,324,443 B1 | 11/2001 | Kurakake et al. |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,346,950 B1 | 2/2002 | Jouppi |
| 6,346,962 B1 | 2/2002 | Goodridge |
| 6,369,847 B1 | 4/2002 | James et al. |
| 6,381,515 B1 | 4/2002 | Inoue et al. |
| 6,400,378 B1 | 6/2002 | Snook |
| 6,408,230 B2 | 6/2002 | Wada |
| 6,430,471 B1 | 8/2002 | Kintou et al. |
| 6,430,475 B2 | 8/2002 | Okamoto et al. |
| 6,438,457 B1 | 8/2002 | Yokoo et al. |
| 6,445,964 B1 | 9/2002 | White et al. |
| 6,449,762 B1 | 9/2002 | McElvain |
| 6,452,915 B1 | 9/2002 | Jorgensen |
| 6,457,043 B1 | 9/2002 | Kwak et al. |

(56) References Cited

U.S. PATENT DOCUMENTS

| | | |
|---|---|---|
| 6,459,955 B1 | 10/2002 | Bartsch et al. |
| 6,463,352 B1 | 10/2002 | Tadokoro et al. |
| 6,463,361 B1 | 10/2002 | Wang et al. |
| 6,466,844 B1 | 10/2002 | Ikeda et al. |
| 6,468,265 B1 | 10/2002 | Evans et al. |
| 6,470,235 B2 | 10/2002 | Kasuga et al. |
| 6,474,434 B1 | 11/2002 | Bech |
| 6,480,762 B1 | 11/2002 | Uchikubo et al. |
| 6,491,701 B2 | 12/2002 | Tierney et al. |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury et al. |
| 6,523,629 B1 | 2/2003 | Buttz et al. |
| 6,526,332 B2 | 2/2003 | Sakamoto et al. |
| 6,529,765 B1 | 3/2003 | Franck et al. |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu et al. |
| 6,543,899 B2 | 4/2003 | Covannon et al. |
| 6,549,215 B2 | 4/2003 | Jouppi |
| 6,563,533 B1 | 5/2003 | Colby |
| 6,580,246 B2 | 6/2003 | Jacobs |
| 6,581,798 B2 | 6/2003 | Liff et al. |
| 6,584,376 B1 | 6/2003 | Van Kommer |
| 6,587,750 B2 | 7/2003 | Gerbi et al. |
| 6,594,269 B1 | 7/2003 | Polcyn |
| 6,594,552 B1 | 7/2003 | Nowlin et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,611,120 B2 | 8/2003 | Song et al. |
| 6,643,496 B1 | 11/2003 | Shimoyama et al. |
| 6,646,677 B2 | 11/2003 | Noro et al. |
| 6,650,748 B1 | 11/2003 | Edwards et al. |
| 6,666,374 B1 | 12/2003 | Green et al. |
| 6,684,129 B2 | 1/2004 | Salisbury et al. |
| 6,691,000 B2 | 2/2004 | Nagai et al. |
| 6,710,797 B1 | 3/2004 | McNelley et al. |
| 6,728,599 B2 | 4/2004 | Wang |
| 6,763,282 B2 | 7/2004 | Glenn et al. |
| 6,764,373 B1 | 7/2004 | Osawa et al. |
| 6,769,771 B2 | 8/2004 | Trumbull |
| 6,781,606 B2 | 8/2004 | Jouppi |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2* | 10/2005 | Ghodoussi et al. ........... 600/101 |
| 6,952,470 B1 | 10/2005 | Tioe et al. |
| 6,957,712 B2 | 10/2005 | Song et al. |
| 6,958,706 B2 | 10/2005 | Chaco et al. |
| 6,965,394 B2 | 11/2005 | Gutta et al. |
| 6,995,664 B1 | 2/2006 | Darling |
| 7,007,235 B1 | 2/2006 | Hussein et al. |
| 7,015,934 B2 | 3/2006 | Toyama et al. |
| RE39,080 E | 4/2006 | Johnston |
| 7,030,757 B2 | 4/2006 | Matsuhira et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | McLurkin et al. |
| 7,123,285 B2 | 10/2006 | Smith et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles |
| 7,142,945 B2 | 11/2006 | Wang et al. |
| 7,142,947 B2 | 11/2006 | Wang et al. |
| 7,151,982 B2 | 12/2006 | Liff et al. |
| 7,154,526 B2 | 12/2006 | Foote et al. |
| 7,155,306 B2 | 12/2006 | Haitin et al. |
| 7,156,809 B2 | 1/2007 | Quy |
| 7,158,859 B2 | 1/2007 | Wang et al. |
| 7,158,860 B2 | 1/2007 | Wang et al. |
| 7,158,861 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,164,970 B2 | 1/2007 | Wang et al. |
| 7,167,448 B2 | 1/2007 | Wookey et al. |
| 7,171,286 B2 | 1/2007 | Wang et al. |
| 7,174,238 B1 | 2/2007 | Zweig |
| 7,181,455 B2 | 2/2007 | Wookey et al. |
| 7,184,559 B2 | 2/2007 | Jouppi |
| 7,188,000 B2 | 3/2007 | Chiappetta et al. |
| 7,199,790 B2 | 4/2007 | Rosenberg et al. |
| 7,202,851 B2 | 4/2007 | Cunningham et al. |
| 7,206,627 B2 | 4/2007 | Abovitz et al. |
| 7,215,786 B2 | 5/2007 | Nakadai |
| 7,227,334 B2 | 6/2007 | Yang et al. |
| 7,256,708 B2 | 8/2007 | Rosenfeld |
| 7,262,573 B2 | 8/2007 | Wang et al. |
| 7,289,883 B2 | 10/2007 | Wang et al. |
| 7,292,912 B2 | 11/2007 | Wang et al. |
| 7,317,685 B1 | 1/2008 | Flott et al. |
| 7,321,807 B2 | 1/2008 | Laski |
| 7,346,429 B2 | 3/2008 | Goldenberg et al. |
| 7,382,399 B1 | 6/2008 | McCall et al. |
| 7,386,730 B2 | 6/2008 | Uchikubo |
| 7,391,432 B2 | 6/2008 | Terada |
| 7,400,578 B2 | 7/2008 | Guthrie et al. |
| 7,404,140 B2 | 7/2008 | O'rourke |
| 7,421,470 B2 | 9/2008 | Ludwig et al. |
| 7,430,209 B2 | 9/2008 | Porter |
| 7,432,949 B2 | 10/2008 | Remy et al. |
| 7,433,921 B2 | 10/2008 | Ludwig et al. |
| 7,441,953 B2 | 10/2008 | Banks |
| 7,492,731 B2 | 2/2009 | Hagendorf |
| 7,523,069 B1 | 4/2009 | Friedl et al. |
| 7,525,281 B2 | 4/2009 | Koyanagi et al. |
| 7,535,486 B2 | 5/2009 | Motomura et al. |
| 7,587,512 B2 | 9/2009 | Ta et al. |
| 7,590,060 B2 | 9/2009 | Miceli |
| 7,593,030 B2 | 9/2009 | Wang et al. |
| 7,599,290 B2 | 10/2009 | Dos Remedios et al. |
| 7,624,166 B2 | 11/2009 | Foote et al. |
| 7,630,314 B2 | 12/2009 | Dos Remedios et al. |
| 7,643,051 B2 | 1/2010 | Sandberg et al. |
| 7,647,320 B2 | 1/2010 | Mok et al. |
| 7,680,038 B1 | 3/2010 | Gourlay |
| 7,693,757 B2 | 4/2010 | Zimmerman |
| 7,698,432 B2 | 4/2010 | Short et al. |
| 7,719,229 B2 | 5/2010 | Kaneko et al. |
| 7,739,383 B1 | 6/2010 | Short et al. |
| 7,756,614 B2 | 7/2010 | Jouppi |
| 7,761,185 B2 | 7/2010 | Wang et al. |
| 7,769,492 B2 | 8/2010 | Wang et al. |
| 7,769,705 B1 | 8/2010 | Luechtefeld |

(56) References Cited

U.S. PATENT DOCUMENTS

| | | | |
|---|---|---|---|
| 7,813,836 B2 | 10/2010 | Wang et al. | |
| 7,831,575 B2 | 11/2010 | Trossell et al. | |
| 7,835,775 B2 | 11/2010 | Sawayama et al. | |
| 7,860,680 B2 | 12/2010 | Arms et al. | |
| 7,890,382 B2 | 2/2011 | Robb et al. | |
| 7,912,583 B2 | 3/2011 | Gutmann et al. | |
| RE42,288 E | 4/2011 | Degioanni | |
| 7,924,323 B2 | 4/2011 | Walker et al. | |
| 7,949,616 B2 | 5/2011 | Levy et al. | |
| 7,982,763 B2 | 7/2011 | King | |
| 7,987,069 B2 | 7/2011 | Rodgers et al. | |
| 8,077,963 B2 | 12/2011 | Wang et al. | |
| 8,116,910 B2 | 2/2012 | Walters et al. | |
| 8,170,241 B2 | 5/2012 | Roe et al. | |
| 8,179,418 B2 | 5/2012 | Wright et al. | |
| 8,180,486 B2 | 5/2012 | Saito et al. | |
| 8,209,051 B2 | 6/2012 | Wang et al. | |
| 8,265,793 B2 | 9/2012 | Cross et al. | |
| 8,292,807 B2 | 10/2012 | Perkins et al. | |
| 8,340,654 B2 | 12/2012 | Bratton et al. | |
| 8,340,819 B2 | 12/2012 | Mangaser et al. | |
| 8,463,435 B2 | 6/2013 | Herzog et al. | |
| 8,503,340 B1 | 8/2013 | Xu | |
| 8,527,094 B2 | 9/2013 | Kumar et al. | |
| 8,532,860 B2 | 9/2013 | Daly | |
| 2001/0002448 A1 | 5/2001 | Wilson et al. | |
| 2001/0010053 A1 | 7/2001 | Ben-Shachar et al. | |
| 2001/0020200 A1 | 9/2001 | Das et al. | |
| 2001/0034475 A1 | 10/2001 | Flach et al. | |
| 2001/0034544 A1 | 10/2001 | Mo | |
| 2001/0037163 A1 | 11/2001 | Allard | |
| 2001/0048464 A1 | 12/2001 | Barnett | |
| 2001/0051881 A1* | 12/2001 | Filler | 705/3 |
| 2001/0054071 A1 | 12/2001 | Loeb | |
| 2001/0055373 A1 | 12/2001 | Yamashita | |
| 2002/0015296 A1 | 2/2002 | Howell | |
| 2002/0027597 A1 | 3/2002 | Sachau | |
| 2002/0027652 A1 | 3/2002 | Paromtchik et al. | |
| 2002/0033880 A1 | 3/2002 | Sul et al. | |
| 2002/0038168 A1 | 3/2002 | Kasuga et al. | |
| 2002/0049517 A1 | 4/2002 | Ruffner | |
| 2002/0055917 A1 | 5/2002 | Muraca | |
| 2002/0057279 A1 | 5/2002 | Jouppi | |
| 2002/0058929 A1 | 5/2002 | Green | |
| 2002/0059587 A1 | 5/2002 | Cofano et al. | |
| 2002/0063726 A1 | 5/2002 | Jouppi | |
| 2002/0073429 A1 | 6/2002 | Beane et al. | |
| 2002/0082498 A1 | 6/2002 | Wendt et al. | |
| 2002/0085030 A1 | 7/2002 | Ghani | |
| 2002/0095238 A1 | 7/2002 | Ahlin et al. | |
| 2002/0095239 A1 | 7/2002 | Wallach et al. | |
| 2002/0098879 A1 | 7/2002 | Rheey | |
| 2002/0104094 A1 | 8/2002 | Alexander et al. | |
| 2002/0109770 A1 | 8/2002 | Terada | |
| 2002/0111988 A1 | 8/2002 | Sato | |
| 2002/0120362 A1 | 8/2002 | Lathan et al. | |
| 2002/0130950 A1 | 9/2002 | James et al. | |
| 2002/0133062 A1 | 9/2002 | Arling et al. | |
| 2002/0141595 A1 | 10/2002 | Jouppi | |
| 2002/0143923 A1 | 10/2002 | Alexander | |
| 2002/0177925 A1 | 11/2002 | Onishi et al. | |
| 2002/0183894 A1 | 12/2002 | Wang et al. | |
| 2002/0184674 A1 | 12/2002 | Xi et al. | |
| 2002/0186243 A1 | 12/2002 | Ellis et al. | |
| 2003/0021107 A1 | 1/2003 | Howell et al. | |
| 2003/0030397 A1 | 2/2003 | Simmons | |
| 2003/0048481 A1 | 3/2003 | Kobayashi et al. | |
| 2003/0050733 A1 | 3/2003 | Wang et al. | |
| 2003/0050734 A1 | 3/2003 | Lapham | |
| 2003/0060808 A1 | 3/2003 | Wilk | |
| 2003/0063600 A1 | 4/2003 | Noma et al. | |
| 2003/0069752 A1 | 4/2003 | Ledain et al. | |
| 2003/0100892 A1 | 5/2003 | Morley et al. | |
| 2003/0104806 A1 | 6/2003 | Ruef et al. | |
| 2003/0114962 A1 | 6/2003 | Niemeyer | |
| 2003/0126361 A1 | 7/2003 | Slater et al. | |
| 2003/0135203 A1 | 7/2003 | Wang et al. | |
| 2003/0144579 A1 | 7/2003 | Buss | |
| 2003/0144649 A1 | 7/2003 | Ghodoussi et al. | |
| 2003/0151658 A1 | 8/2003 | Smith | |
| 2003/0152145 A1 | 8/2003 | Kawakita | |
| 2003/0171710 A1 | 9/2003 | Bassuk et al. | |
| 2003/0174285 A1 | 9/2003 | Trumbull | |
| 2003/0180697 A1 | 9/2003 | Kim et al. | |
| 2003/0199000 A1 | 10/2003 | Valkirs et al. | |
| 2003/0206242 A1 | 11/2003 | Choi | |
| 2003/0212472 A1 | 11/2003 | McKee | |
| 2003/0216834 A1 | 11/2003 | Allard | |
| 2003/0220541 A1 | 11/2003 | Salisbury et al. | |
| 2003/0220715 A1 | 11/2003 | Kneifel, II et al. | |
| 2003/0231244 A1 | 12/2003 | Bonilla et al. | |
| 2003/0232649 A1 | 12/2003 | Gizis et al. | |
| 2003/0236590 A1 | 12/2003 | Park et al. | |
| 2004/0001197 A1 | 1/2004 | Ko et al. | |
| 2004/0001676 A1 | 1/2004 | Colgan et al. | |
| 2004/0010344 A1 | 1/2004 | Hiratsuka et al. | |
| 2004/0012362 A1 | 1/2004 | Tsurumi | |
| 2004/0013295 A1 | 1/2004 | Sabe et al. | |
| 2004/0019406 A1* | 1/2004 | Wang et al. | 700/231 |
| 2004/0024490 A1 | 2/2004 | McLurkin et al. | |
| 2004/0041904 A1 | 3/2004 | Lapalme et al. | |
| 2004/0065073 A1 | 4/2004 | Nash | |
| 2004/0068657 A1 | 4/2004 | Alexander et al. | |
| 2004/0078219 A1 | 4/2004 | Kaylor et al. | |
| 2004/0080610 A1 | 4/2004 | James et al. | |
| 2004/0088077 A1 | 5/2004 | Jouppi et al. | |
| 2004/0093409 A1 | 5/2004 | Thompson et al. | |
| 2004/0095516 A1 | 5/2004 | Rohlicek | |
| 2004/0098167 A1 | 5/2004 | Yi et al. | |
| 2004/0102167 A1 | 5/2004 | Shim et al. | |
| 2004/0107254 A1 | 6/2004 | Ludwig et al. | |
| 2004/0107255 A1 | 6/2004 | Ludwig et al. | |
| 2004/0117065 A1* | 6/2004 | Wang et al. | 700/245 |
| 2004/0123158 A1 | 6/2004 | Roskind | |
| 2004/0135879 A1 | 7/2004 | Stacy et al. | |
| 2004/0138547 A1 | 7/2004 | Wang et al. | |
| 2004/0143421 A1 | 7/2004 | Wang et al. | |
| 2004/0148638 A1 | 7/2004 | Weisman et al. | |
| 2004/0153211 A1 | 8/2004 | Kamoto et al. | |
| 2004/0157612 A1 | 8/2004 | Kim | |
| 2004/0162637 A1 | 8/2004 | Wang et al. | |
| 2004/0167666 A1 | 8/2004 | Wang et al. | |
| 2004/0167668 A1 | 8/2004 | Wang et al. | |
| 2004/0170300 A1 | 9/2004 | Jouppi | |
| 2004/0172301 A1 | 9/2004 | Mihai et al. | |
| 2004/0172306 A1 | 9/2004 | Wohl et al. | |
| 2004/0174129 A1 | 9/2004 | Wang et al. | |
| 2004/0175684 A1 | 9/2004 | Kaasa et al. | |
| 2004/0179714 A1 | 9/2004 | Jouppi et al. | |
| 2004/0186623 A1 | 9/2004 | Dooley et al. | |
| 2004/0189700 A1 | 9/2004 | Mandavilli et al. | |
| 2004/0201602 A1 | 10/2004 | Mody et al. | |
| 2004/0205664 A1 | 10/2004 | Prendergast | |
| 2004/0215490 A1 | 10/2004 | Duchon et al. | |
| 2004/0222638 A1 | 11/2004 | Bednyak | |
| 2004/0224676 A1 | 11/2004 | Iseki | |
| 2004/0230340 A1 | 11/2004 | Fukuchi et al. | |
| 2004/0240981 A1 | 12/2004 | Dothan et al. | |
| 2004/0241981 A1 | 12/2004 | Doris et al. | |
| 2005/0003330 A1 | 1/2005 | Asgarinejad | |
| 2005/0004708 A1 | 1/2005 | Goldenberg et al. | |
| 2005/0007445 A1 | 1/2005 | Foote et al. | |
| 2005/0013149 A1 | 1/2005 | Trossell | |
| 2005/0021182 A1 | 1/2005 | Wang et al. | |
| 2005/0021183 A1 | 1/2005 | Wang et al. | |
| 2005/0021187 A1 | 1/2005 | Wang et al. | |
| 2005/0021309 A1 | 1/2005 | Alexander et al. | |
| 2005/0024485 A1 | 2/2005 | Castles et al. | |
| 2005/0027567 A1 | 2/2005 | Taha | |
| 2005/0027794 A1 | 2/2005 | Decker | |
| 2005/0028221 A1 | 2/2005 | Liu et al. | |
| 2005/0035862 A1 | 2/2005 | Wildman et al. | |
| 2005/0038416 A1 | 2/2005 | Wang et al. | |
| 2005/0038564 A1 | 2/2005 | Burick et al. | |

(56) References Cited

U.S. PATENT DOCUMENTS

| | | | |
|---|---|---|---|
| 2005/0049898 A1 | 3/2005 | Hirakawa | |
| 2005/0052527 A1* | 3/2005 | Remy et al. | 348/14.08 |
| 2005/0060211 A1 | 3/2005 | Xiao et al. | |
| 2005/0065435 A1 | 3/2005 | Rauch et al. | |
| 2005/0065438 A1 | 3/2005 | Miller | |
| 2005/0065659 A1 | 3/2005 | Tanaka et al. | |
| 2005/0065813 A1 | 3/2005 | Mishelevich et al. | |
| 2005/0071046 A1 | 3/2005 | Miyazaki et al. | |
| 2005/0078816 A1 | 4/2005 | Sekiguchi et al. | |
| 2005/0083011 A1 | 4/2005 | Yang et al. | |
| 2005/0099493 A1 | 5/2005 | Chew | |
| 2005/0104964 A1 | 5/2005 | Bovyrin et al. | |
| 2005/0110867 A1 | 5/2005 | Schulz | |
| 2005/0122390 A1 | 6/2005 | Wang et al. | |
| 2005/0125098 A1 | 6/2005 | Wang et al. | |
| 2005/0154265 A1 | 7/2005 | Miro et al. | |
| 2005/0182322 A1 | 8/2005 | Grispo | |
| 2005/0192721 A1 | 9/2005 | Jouppi | |
| 2005/0204438 A1 | 9/2005 | Wang et al. | |
| 2005/0212478 A1 | 9/2005 | Takenaka | |
| 2005/0219356 A1 | 10/2005 | Smith et al. | |
| 2005/0225634 A1 | 10/2005 | Brunetti et al. | |
| 2005/0231156 A1 | 10/2005 | Yan | |
| 2005/0231586 A1 | 10/2005 | Rodman et al. | |
| 2005/0232647 A1 | 10/2005 | Takenaka | |
| 2005/0234592 A1 | 10/2005 | McGee et al. | |
| 2005/0267826 A1 | 12/2005 | Levy et al. | |
| 2005/0283414 A1 | 12/2005 | Fernandes et al. | |
| 2006/0007943 A1 | 1/2006 | Fellman | |
| 2006/0013263 A1 | 1/2006 | Fellman | |
| 2006/0013469 A1 | 1/2006 | Wang et al. | |
| 2006/0013488 A1 | 1/2006 | Inoue | |
| 2006/0014388 A1 | 1/2006 | Lur et al. | |
| 2006/0020694 A1 | 1/2006 | Nag et al. | |
| 2006/0029065 A1 | 2/2006 | Fellman | |
| 2006/0047365 A1 | 3/2006 | Ghodoussi et al. | |
| 2006/0048286 A1 | 3/2006 | Donato | |
| 2006/0052676 A1 | 3/2006 | Wang et al. | |
| 2006/0052684 A1 | 3/2006 | Takahashi et al. | |
| 2006/0064212 A1 | 3/2006 | Thorne | |
| 2006/0074525 A1 | 4/2006 | Close et al. | |
| 2006/0074719 A1 | 4/2006 | Horner | |
| 2006/0082642 A1 | 4/2006 | Wang et al. | |
| 2006/0087746 A1 | 4/2006 | Lipow | |
| 2006/0095158 A1 | 5/2006 | Lee et al. | |
| 2006/0095170 A1 | 5/2006 | Yang et al. | |
| 2006/0098573 A1 | 5/2006 | Beer et al. | |
| 2006/0103659 A1 | 5/2006 | Karandikar et al. | |
| 2006/0104279 A1 | 5/2006 | Fellman et al. | |
| 2006/0106493 A1 | 5/2006 | Niemeyer et al. | |
| 2006/0122482 A1 | 6/2006 | Mariotti et al. | |
| 2006/0125356 A1 | 6/2006 | Meek, Jr. et al. | |
| 2006/0142983 A1 | 6/2006 | Sorensen | |
| 2006/0149418 A1 | 7/2006 | Anvari | |
| 2006/0161136 A1 | 7/2006 | Anderson et al. | |
| 2006/0161303 A1 | 7/2006 | Wang et al. | |
| 2006/0164546 A1 | 7/2006 | Adachi | |
| 2006/0171515 A1 | 8/2006 | Hintermeister et al. | |
| 2006/0173708 A1 | 8/2006 | Vining et al. | |
| 2006/0173712 A1 | 8/2006 | Joubert | |
| 2006/0178776 A1 | 8/2006 | Feingold et al. | |
| 2006/0178777 A1 | 8/2006 | Park et al. | |
| 2006/0189393 A1 | 8/2006 | Edery | |
| 2006/0195569 A1 | 8/2006 | Barker | |
| 2006/0224781 A1 | 10/2006 | Tsao et al. | |
| 2006/0247045 A1 | 11/2006 | Jeong et al. | |
| 2006/0259193 A1 | 11/2006 | Wang et al. | |
| 2006/0268704 A1 | 11/2006 | Ansari et al. | |
| 2006/0271238 A1 | 11/2006 | Choi et al. | |
| 2006/0271400 A1 | 11/2006 | Clements et al. | |
| 2006/0293788 A1 | 12/2006 | Pogodin | |
| 2007/0021871 A1 | 1/2007 | Wang et al. | |
| 2007/0025711 A1 | 2/2007 | Marcus | |
| 2007/0046237 A1 | 3/2007 | Lakshmanan et al. | |
| 2007/0050937 A1 | 3/2007 | Song et al. | |
| 2007/0064092 A1 | 3/2007 | Sandbeg et al. | |
| 2007/0078566 A1 | 4/2007 | Wang et al. | |
| 2007/0112700 A1 | 5/2007 | Den et al. | |
| 2007/0117516 A1 | 5/2007 | Saidi et al. | |
| 2007/0120965 A1 | 5/2007 | Sandberg et al. | |
| 2007/0122783 A1 | 5/2007 | Habashi | |
| 2007/0133407 A1 | 6/2007 | Choi et al. | |
| 2007/0135967 A1 | 6/2007 | Jung et al. | |
| 2007/0142964 A1 | 6/2007 | Abramson | |
| 2007/0176060 A1 | 8/2007 | White et al. | |
| 2007/0192910 A1 | 8/2007 | Vu et al. | |
| 2007/0197896 A1 | 8/2007 | Moll et al. | |
| 2007/0198128 A1 | 8/2007 | Ziegler et al. | |
| 2007/0198130 A1 | 8/2007 | Wang et al. | |
| 2007/0199108 A1 | 8/2007 | Angle et al. | |
| 2007/0216347 A1 | 9/2007 | Kaneko et al. | |
| 2007/0250212 A1 | 10/2007 | Halloran et al. | |
| 2007/0255706 A1 | 11/2007 | Iketani et al. | |
| 2007/0262884 A1 | 11/2007 | Goncalves et al. | |
| 2007/0273751 A1 | 11/2007 | Sachau | |
| 2007/0291109 A1 | 12/2007 | Wang et al. | |
| 2007/0291128 A1 | 12/2007 | Wang et al. | |
| 2008/0009969 A1 | 1/2008 | Bruemmer et al. | |
| 2008/0011904 A1 | 1/2008 | Cepollina et al. | |
| 2008/0045804 A1 | 2/2008 | Williams | |
| 2008/0065268 A1 | 3/2008 | Wang et al. | |
| 2008/0082211 A1 | 4/2008 | Wang et al. | |
| 2008/0126132 A1 | 5/2008 | Warner et al. | |
| 2008/0133052 A1 | 6/2008 | Jones et al. | |
| 2008/0174570 A1 | 7/2008 | Jobs et al. | |
| 2008/0201016 A1 | 8/2008 | Finlay | |
| 2008/0201017 A1 | 8/2008 | Wang et al. | |
| 2008/0215987 A1 | 9/2008 | Alexander et al. | |
| 2008/0229531 A1 | 9/2008 | Takida | |
| 2008/0255703 A1 | 10/2008 | Wang et al. | |
| 2008/0263451 A1 | 10/2008 | Portele et al. | |
| 2008/0269949 A1 | 10/2008 | Norman et al. | |
| 2008/0281467 A1 | 11/2008 | Pinter | |
| 2008/0306375 A1 | 12/2008 | Sayler et al. | |
| 2009/0030552 A1 | 1/2009 | Nakadai et al. | |
| 2009/0044334 A1 | 2/2009 | Parsell et al. | |
| 2009/0055023 A1 | 2/2009 | Walters et al. | |
| 2009/0070135 A1 | 3/2009 | Parida et al. | |
| 2009/0086013 A1 | 4/2009 | Thapa | |
| 2009/0105882 A1 | 4/2009 | Wang et al. | |
| 2009/0106679 A1 | 4/2009 | Anzures et al. | |
| 2009/0122699 A1 | 5/2009 | Alperovitch et al. | |
| 2009/0125147 A1 | 5/2009 | Wang et al. | |
| 2009/0144425 A1 | 6/2009 | Marr et al. | |
| 2009/0164255 A1 | 6/2009 | Menschik et al. | |
| 2009/0164657 A1 | 6/2009 | Li et al. | |
| 2009/0171170 A1 | 7/2009 | Li et al. | |
| 2009/0177323 A1 | 7/2009 | Ziegler et al. | |
| 2009/0177641 A1 | 7/2009 | Raghavan | |
| 2009/0237317 A1 | 9/2009 | Rofougaran | |
| 2009/0240371 A1 | 9/2009 | Wang et al. | |
| 2009/0248200 A1 | 10/2009 | Root | |
| 2009/0259339 A1 | 10/2009 | Wright et al. | |
| 2010/0010672 A1 | 1/2010 | Wang et al. | |
| 2010/0010673 A1 | 1/2010 | Wang et al. | |
| 2010/0019715 A1 | 1/2010 | Roe et al. | |
| 2010/0051596 A1 | 3/2010 | Diedrick et al. | |
| 2010/0063848 A1 | 3/2010 | Kremer et al. | |
| 2010/0070079 A1 | 3/2010 | Mangaser et al. | |
| 2010/0073490 A1 | 3/2010 | Wang et al. | |
| 2010/0076600 A1 | 3/2010 | Cross et al. | |
| 2010/0085874 A1 | 4/2010 | Noy et al. | |
| 2010/0088232 A1 | 4/2010 | Gale | |
| 2010/0115418 A1 | 5/2010 | Wang et al. | |
| 2010/0116566 A1 | 5/2010 | Ohm et al. | |
| 2010/0131103 A1 | 5/2010 | Herzog et al. | |
| 2010/0145479 A1 | 6/2010 | Griffiths | |
| 2010/0157825 A1 | 6/2010 | Anderlind et al. | |
| 2010/0191375 A1 | 7/2010 | Wright et al. | |
| 2010/0228249 A1 | 9/2010 | Mohr et al. | |
| 2010/0268383 A1 | 10/2010 | Wang et al. | |
| 2010/0323783 A1 | 12/2010 | Nonaka et al. | |
| 2011/0050841 A1 | 3/2011 | Wang et al. | |
| 2011/0071702 A1 | 3/2011 | Wang et al. | |

(56) References Cited

U.S. PATENT DOCUMENTS

| | | | |
|---|---|---|---|
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0213210 A1 | 9/2011 | Temby et al. |
| 2011/0218674 A1 | 9/2011 | Stuart et al. |
| 2011/0245973 A1 | 10/2011 | Wang et al. |
| 2011/0292193 A1 | 12/2011 | Wang et al. |
| 2011/0301759 A1 | 12/2011 | Wang et al. |
| 2012/0023506 A1 | 1/2012 | Maeckel et al. |
| 2012/0036484 A1 | 2/2012 | Zhang et al. |
| 2012/0072023 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0191246 A1 | 7/2012 | Roe et al. |
| 2012/0191464 A1 | 7/2012 | Stuart et al. |

FOREIGN PATENT DOCUMENTS

| | | |
|---|---|---|
| CN | 1554193 A | 12/2004 |
| CN | 1554985 A | 12/2004 |
| CN | 101106939 A | 1/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 466492 A2 | 1/1992 |
| EP | 488673 A2 | 6/1992 |
| EP | 0981905 B1 | 1/2002 |
| EP | 1 262 142 A2 | 12/2002 |
| EP | 1304872 A1 | 4/2003 |
| EP | 1 536 660 B2 | 9/2004 |
| EP | 1 536 660 A2 | 6/2005 |
| EP | 1573406 A2 | 9/2005 |
| EP | 1594660 A2 | 11/2005 |
| EP | 1763243 A2 | 3/2007 |
| EP | 1791464 A2 | 6/2007 |
| EP | 1800476 A2 | 6/2007 |
| EP | 1819108 A2 | 8/2007 |
| EP | 1856644 A2 | 11/2007 |
| EP | 1536660 A3 | 4/2008 |
| EP | 1928310 A2 | 6/2008 |
| EP | 1232610 B1 | 1/2009 |
| EP | 2027716 A2 | 2/2009 |
| EP | 2145274 A1 | 1/2010 |
| EP | 2214111 A2 | 8/2010 |
| EP | 2263158 A2 | 12/2010 |
| EP | 2300930 A1 | 3/2011 |
| EP | 2342651 A1 | 7/2011 |
| GB | 2431261 A | 4/2007 |
| JP | 07-194609 A | 8/1995 |
| JP | 2007-213753 A | 8/1995 |
| JP | 2007-248823 A | 8/1995 |
| JP | 07-257422 A | 10/1995 |
| JP | 08-084328 A | 3/1996 |
| JP | 8320727 A | 12/1996 |
| JP | 9-267276 A | 10/1997 |
| JP | 1079097 A | 3/1998 |
| JP | 10288689 A | 10/1998 |
| JP | 2000-032319 A | 1/2000 |
| JP | 2000049800 A | 2/2000 |
| JP | 2000079587 A | 3/2000 |
| JP | 2000196876 A | 7/2000 |
| JP | 2000-235423 A | 8/2000 |
| JP | 2001-147718 A | 5/2001 |
| JP | 2001125641 A | 5/2001 |
| JP | 2001-198865 A | 7/2001 |
| JP | 2001 198868 A | 7/2001 |
| JP | 2001-199356 A | 7/2001 |
| JP | 2001179663 A | 7/2001 |
| JP | 2000-188124 | 1/2002 |
| JP | 2002-000574 A | 1/2002 |
| JP | 2002-046088 A | 2/2002 |
| JP | 2002101333 A | 4/2002 |
| JP | 2002112970 A | 4/2002 |
| JP | 2002-305743 A | 10/2002 |
| JP | 2002-355779 A | 12/2002 |
| JP | 2004524824 T | 8/2004 |
| JP | 2004261941 A | 9/2004 |
| JP | 2004289379 A | 10/2004 |
| JP | 2005028066 A | 2/2005 |
| JP | 2005059170 A | 3/2005 |
| JP | 2006508806 A | 3/2006 |
| JP | 2006109094 A | 4/2006 |
| JP | 2006224294 A | 8/2006 |
| JP | 2006246438 A | 9/2006 |
| JP | 2007007040 A | 1/2007 |
| JP | 2007081646 A | 3/2007 |
| JP | 2007232208 A | 9/2007 |
| JP | 2007316966 A | 12/2007 |
| JP | 2010064154 A | 3/2010 |
| JP | 2010532109 A | 9/2010 |
| JP | 2010246954 A | 11/2010 |
| KR | 20060037979 A | 5/2006 |
| KR | 20090012542 A | 2/2009 |
| KR | 20100019479 A | 2/2010 |
| KR | 20100139037 A | 12/2010 |
| WO | WO 93/06690 A1 | 4/1993 |
| WO | WO 98/51078 A | 11/1998 |
| WO | WO 99/67067 A1 | 12/1999 |
| WO | 00/25516 A1 | 5/2000 |
| WO | 00/33726 A1 | 6/2000 |
| WO | 01/31861 A1 | 5/2001 |
| WO | WO 03/077745 A | 9/2003 |
| WO | 2004/008738 A1 | 1/2004 |
| WO | 2004/012018 A2 | 2/2004 |
| WO | WO 2004/075456 A2 | 9/2004 |
| WO | 2006/012797 A1 | 2/2006 |
| WO | 2006/044847 A2 | 4/2006 |
| WO | 2006/078611 A2 | 7/2006 |
| WO | 2007/041295 A2 | 4/2007 |
| WO | WO 2007/041295 A1 | 4/2007 |
| WO | 2007/041038 A3 | 6/2007 |
| WO | 2008/100272 A2 | 8/2008 |
| WO | 2008/100272 A3 | 10/2008 |
| WO | 2009/117274 A2 | 9/2009 |
| WO | 2009/128997 A1 | 10/2009 |
| WO | 2009/145958 A2 | 12/2009 |
| WO | 2010/006205 A1 | 1/2010 |
| WO | 2010/006211 A1 | 1/2010 |
| WO | 2010/033666 A1 | 3/2010 |
| WO | 2010/047881 A1 | 4/2010 |
| WO | 2010/062798 A1 | 6/2010 |
| WO | 2010/065257 A1 | 6/2010 |
| WO | 2010/120407 A1 | 10/2010 |
| WO | 2011/028589 A2 | 3/2011 |
| WO | 2011/028589 A3 | 4/2011 |
| WO | 2011/097130 A2 | 8/2011 |
| WO | 2011/097132 A2 | 8/2011 |
| WO | 2011/109336 A2 | 9/2011 |
| WO | 2011/097132 A3 | 12/2011 |
| WO | 2011/149902 A2 | 12/2011 |

OTHER PUBLICATIONS

Han, et al., "Construction of an Omnidirectional Mobile Robot Platform Based on Active Dual-Wheel Caster Mechanisms and Development of a Control Simulator", 2000, Kluwer Acedemic Publishers, vol. 29, pp. 257-275.

Haule et al., "Control Scheme for Delayed Teleoperation Tasks", May 17, 1995, Proceedings of the Pacific Rim Conference on Communications, Computer and Signal Processing.

Lee et al., "A novel method of surgical instruction: International telementoring", 1998, Internet pp. 1-4.

Linebarger, John M. et al., "Concurrency Control Mechanisms for Closely Coupled Collaboration in Multithreaded Virtual Environments", Presence, Special Issue on Advances in Collaborative VEs (2004).

(56) References Cited

OTHER PUBLICATIONS

Ogata et al., "Emotional Communication Robot: WAMOEBA-2R—Emotion Model and Evaluation Experiments", 1999, Internet, pp. 1-16.
Rovetta et al., "A New Telerobotic Application: Remote Laparoscopic Surgery Using Satellites and Optical Fiber Networks for Data Exchange", Jun. 1, 1996, International Journal of Robotics Research, pp. 267-279.
Al-Kassab, "A Review of Telemedicine", Journal of Telemedicine and Telecare, 1999, vol. 5, Supplement 1.
F. Ando et al., "A Multimedia Self-service Terminal with Conferencing Functions", 1995, IEEE, pp. 357-362.
Android Amusement Corp., "What Marketing Secret", 1982 http:///www.theoldrobots.com/images17/dc8.JPG.
Applebome, "Planning Domesticated Robots for Tomorrow's Household", New York Times, Mar. 4, 1982, pp. 21 and 23 http://www.theoldrobots.com/images17/dc17.JPG.
Baltus et al., "Towards Personal Service Robots for the Elderly, Proceedings for the Elderly Workshop on Interactive Robots and Entertainment", 2000, Computer Science and Robotics, http://www.cs.cmu.edu/thrun/papers/thrun.nursebot-early.pdf.
Bar-Cohen et al., Virtual reality robotic telesurgery simulations using MEMICA haptic system, Mar. 5, 2001, Internet, pp. 1-7.
Bartholomew, "An Apothecary's Pharmacy", 1230-1240 http://classes.bnf.fr/ema/grands/034.htm.
Bauer, Jeffrey C., "Service Robots in Health Care: The Evolution of Mechanical Solutions to Human Resource Problems", Jun. 2003.
Bauer, John et al., "Remote telesurgical mentoring: feasibility and efficacy", 2000, IEEE, pp. 1-9.
Bischoff, "Design Concept and Realization of the Humanoid Service Robot HERMES", Field and Service Robotics, Springer, London, 1998, pp. 485-492.
Blackwell, Gerry, "Video: A Wireless LAN Killer App?", 2002, Internet pp. 1-3.
Breslow, Michael J., MD et al., "Effect of a multiple-site intensive care unit telemedicine program on clinical and economic outcome: An alternative paradigm for intensivist staffing", Critical Care Med, Jan. 2004, vol. 32, No. 1, pp. 31-38.
Brooks, Rodney, Abstracts from Flesh & Machines, How Robots Will Change Us, "Remote Presence", p. 131-147, Feb. 2002.
Candelas Herias, F.A. et al., "Flexible virtual and remote laboratory for teaching Robotics", FORMATEX 2006, Proc. Advance in Control Education, Madrid, Spain, Jun. 21-23, 2006.
Celi et al., "The eICU: It's not just telemedicine", Critical Care Medicine, vol. 29, No. 8 (Supplement), Aug. 2001.
Cheetham, Anastasia et al., "Interface Development for a Child's Video Conferencing Robot", 2000, pp. 1-4.
Cleary et al., "State of the art in surgical robotics: Clinical applications and technology challenges", Feb. 24, 2002 Internet, pp. 1-26.
CNN, "Floating 'droids' to roam space corridors of the future", Jan. 12, 2000, Internet, pp. 1-4.
CNN.com/Technology,"Paging R.Robot: Machine helps doctors with patients", Sep. 30, 2003, Internet, 1-3.
Crowley, "Hello to Our Future", AARP Bulletin, Jan. 2000 http://www.cs.cmu.ed/-nursebot/web/press/aarp_99_14/millennium.html.
Dalton, "Techniques for Web Telerobotics", PhD thesis, University of Western Australia, 2001, http://telerobot.mech.uwa.edu.au/information.html, http://catalogue.library.uwa.edu.au/search.
Davies, "Robotics in Minimally Invasive Surgery", 1995, Internet, pp. 5/1-5/2.
Digiorgio, James, "Is Your Emergency Department of the 'Leading Edge'?", 2005, Internet, pp. 1-4.
Discovery Channel Canada, "Inventing the Future: 2000 Years of Discovery", Jan. 2, 2000 (Video/Transcript).
Elhajj et al., "Supermedia in Internet-based telerobotic operations", 2001, Internet, pp. 1-14.
Elhajj et al., "Synchronization and Control of Supermedia Transmission Via the Internet", Proceedings of 2001 International Symposium on Intelligent Multimedia, Video and Speech Processing, May 2-4, 2001, Hong Kong.
Ellison et al., "Telerounding and Patient Satisfaction Following Surgery".
Fels, "Developing a Video-Mediated Communication System for Hospitalized Children", Telemedicine Journal, vol. 5, No. 2, 1999.
Fetterman, Videoconferencing over the Internet, 2001, Internet, pp. 1-8.
Fiorini, "Health Care Robotics: A Progress Report, IEEE International Conference on Robotics and Automation", 1997.
Ghiasi, "A Generic Web-based Teleoperations Architecture: Details and Experience", SPIE Conference on Telemanipulator and Telepresence Technologies VI, Sep. 1999.
Goldberg et al., "Collaborative Teleoperation via the Internet", IEEE International Conference on Robotics and Automation, Apr. 2000, San Francisco, California.
Goldberg, "Desktop Teleoperation via the World Wide Web, Proceedings of the IEEE International Conference on Robotics and Automation", 1995, http://citeseer.ist.psu.edu/cache/papers/cs/5/ftp:zSzzSzusc.eduzSzpubzSziriszSzraiders.pdf/gol.
Goldberg, "More Online Robots, Robots that Manipulate", Internet, Updated Aug. 2001 http://ford.ieor.berkeley.edu/ir/robots_a2.html.
Goldman, Lea, "Machine Dreams", Entrepreneurs, Forbes, May 27, 2002.
Gump, Michael D., "Robot Technology Improves VA Pharmacies", 2001, Internet, pp. 1-3.
Handley, "RFC 2327—SDP: Session Description Protocol", Apr. 1998 http://www.faqs.org/rfcs/rfc2327.html.
Hanebeck, "ROMAN: a mobile Robotic Assistant for Indoor Service Applications", Proceedings of the 1997 IEEE/RSJ International Conference on Intelligent Robots and Systems, 1997.
Harmo et al., "Moving Eye—Interactive Telepresence Over Internet With a Ball Shaped Mobile Robot", 2000.
Hees, William P., "Communications Design for a Remote Presence Robot", Jan. 14, 2002.
Holmberg, "Development of a Holonomic Mobile Robot for Mobile Manipulation Tasks", International Conference on Field and Service Robotics, Pittsburgh, PA, Aug. 1999.
Ishiguro, "Integrating a Perceptual Information Infrastructure with Robotic Avatars: A Framework for Tele-Existence" Proceeding of IEEE Conference on Intelligent Robots and Systems, http://www.ai.soc.i.kyoto-u.ac.jp/services/publications/99/99conf/07.pdf.
Ishihara, Ken et al., "Intelligent Microrobot DDS (Drug Delivery System) Measured and Controlled by Ultrasonics", Nov. 3-5, 1991, IEEE/RSJ, pp. 1145-1150, vol. 2.
ITU, "ITU-T H.323 Packet-based multimedia communications", ITU, Feb. 1998, http://www.itu.int/rec/T-REC-H.323-199802-S/en.
Ivanova, Natali, "Master's thesis: Internet Based Interface for Control of a Mobile Robot", Department of Numerical Analysis and Computer Science.
Jenkins, "Telehealth Advancing Nursing Practice", Nursing Outlook, Mar./Apr. 2001, vol. 49, No. 2.
Johanson, Supporting video-mediated communication over the Internet, Chalmers University of Technology, Dept of Computer Engineering, Gothenburg, Sweden, 2003.
Jouppi, et al., "Mutually-Immersive Audio Telepresence", Audio Engineering Society Convention Paper, presented at 113th Convention Oct. 2002.
Jouppi, Norman P., "First Steps Towards Mutually-Immersive Mobile Telepresence", CSCW '02, Nov. 16-20, 2002, New Orleans LA.
Kanehiro, Fumio et al., Virtual Humanoid Robot Platform to Develop Controllers of Real Humanoid Robots without Porting, 2001, IEEE, pp. 3217-3276.
Kaplan et al., "An Internet Accessible Telepresence".
Keller et al., "Raven Interface Project", Fall 2001 http://upclose.lrdc.pitt.edu/people/louw_assets/Raven_Slides.pps.
Khatib, "Robots in Human Environments", Proc. International Conference on Control, Automation, Robotics, and Vision, ICRACV2000, Dec. 2000, Singapore, pp. 454-457.
Kuzuoka et al., "Can the GestureCam Be a Surrogate?".

(56) References Cited

OTHER PUBLICATIONS

Lane, "Automated Aides", Newsday, Oct. 17, 2000, http://www.cs.cum.edu/-nursebot/web/press/nd4380.htm.

Lim, Hun-ok et al., Control to Realize Human-like Walking of a Biped Humanoid Robot, IEEE 2000, pp. 3271-3276.

Loeb, Gerald, "Virtual Visit: Improving Communication for Those Who Need It Most", 2001.

Long, "HelpMate Robotics, Inc. (Formerly Transitions Research Corporation) Robot Navigation Technology", NIST Special Publication 950-1, Mar. 1999, http://www.atp.nist.gov/eao/sp950-1/helpmate.htm.

Luna, Nancy, "Robot a new face on geriatric care", OC Register, Aug. 6, 2003.

Mack, "Minimally invasive and robotic surgery", 2001, Internet IEEE, pp. 568-572.

Mair, Telepresence—The Technology and Its Economic and Social Implications, IEEE Technology and Society, 1997.

Martin, Anya, "Days Ahead", Assisted Living Today, vol. 9, Nov./Dec. 2002, pp. 19-22.

McCardle et al., "The challenge of utilizing new technology in design education", 2000 Internet, pp. 122-127.

Meng, "E-Service Robot in Home Healthcare", Proceedings of the 2000, IEEE/RSJ, International Conference on Intelligent Robots and Systems, 2000.

Michaud, Introducing 'Nursebot', The Boston Globe, Sep. 11, 2001, pp. 1-5, http://www.cs.cmu.edu/nursebot/web/press/globe_3_01/index.html.

Mobile Robotics Research Group, "Mobile Robotics Research Group", 2000 Internet, pp. 1-2, Edinburgh.

Montemerlo, "Telepresence: Experiments in Next Generation Internet", CMU Robotics Institute, Oct. 20, 1998, http://www.ri.cmu.edu/creative/archives.htm (Video/Transcript).

Murphy, "Introduction to A1 Robotics", 2000.

Nakajima et al., "A Multimedia Teleteaching System sing an Electronic Whiteboard for Two-Way Communication of Motion Videos and Chalkboards", 1993, IEEE, pp. 436-441.

"National Energy Research Scientific Computing Center, Berkeley Lab's RAGE Telepresence Robot Captures R&D100 Award", Jul. 2, 2002, http://www.nersc.gov/news/newsroom/RAGE070202.php.

Nomadic Technologies, Inc., "Nomad XR4000 Hardware Manual", Mar. 1999.

Ogata et al., "Development of Emotional Communication Robot: WAMOEBA-2r—Esperimental evaluation . . . ", 2000 IEEE, pp. 175-180.

Oh, "Autonomous Battery Recharging for Indoor Mobile Robots", Proceedings of Australian Conference on Robotics and Automation, 2000, http://users.rsise.anu.edu.au/rsl/rsl_papers/ACRA2000/Auto_Recharge_Paper.pdf.

Ojha, Anad, "An application of Virtual Reality in Rehabilitation", Jan. 1994, IEEE, pp. 4-6.

Paulos et al., "A World Wide Web Telerobotic Remote Environment Browser", http://vive.cs.berkeley.edu/capek, 1995.

Paulos, "Designing Personal Tele-embodiment", IEEE International Conference on Robotics and Automation, 1998, http://www.prop.org/papers/icra98.pdf.

Paulos, Eric John, "Personal Tele-Embodiment", UC Berkeley, Fall 2001.

Paulos, "PRoP: Personal Roving Presence", ACM:CHI Proceedings of CHI '98, http://www.prop.org/papers/chi98.pdf.

Paulos, Video of PRoP 2 at Richmond Field Station, www.prop.org. May 2001, Printout of Home Page of Website and two-page Transcript of the audio portion of said PRoP Video.

Paulos, et al., "Ubiquitous Tele-embodiment: Applications and Implications", International Journal of Human Computer Studies, Jun. 1997, vol. 46, No. 6, pp. 861-877.

Pin et al., "A New Family of Omnidirectional and Holonomic Wheeled Platforms for Mobile Robots", IEEE, vol. 10, No. 4, Aug. 1994.

Roy et al., "Towards Personal Service Robots for the Elderly", Internet, Mar. 7, 2002.

Salemi et al, "MILO: Personal robot platform", 2005, Internet, pp. 1-6.

Sandt, Frederic et al., "Perceptions for a Transport Robot in Public Environments", 1997, IROS '97.

Schaeffer, "Care-O-bot: A System for Assisting Elderly or Disabled Persons in Home Environments", Proceedings of AAATE-99, 1999, http://morpha.de/download/publications/IPA_Systems_For_AssistingElderly_or_DisabledPersons_AAATE1999.pdf.

Schultz, "Web Interfaces for Mobile Robots in Public Places", Robotics & Automation magazine, IEEE, vol. 7, Issue 1, Mar. 2000.

Shimoga et al., Touch and force reflection for telepresence surgery, 1994, IEEE, pp. 1049-1050.

Siegwart, "Interacting Mobile Robots on the Web", Proceedings of the 1999 IEEE International Conference on Robotics and Automation, May 1999.

Simmons, "Xavier: An Autonomous Mobile Robot on the Web", IEE robotics and Automation Magazine, 1999, pp. 43-48.

Spawar Systems Center, "Robart", 1998, San Diego, CA, http://web.archive.org/web/*/http://www.nosc.mil/robots/land/robart/robart.html http://web.archive.org/web/19981202205636/http://www.nosc.mil/robots/land/robart/robart.html.

Stephenson, Gary, "Dr. Robot Tested at Hopkins", Aug. 5, 2003, Internet, pp. 1-2.

Stoianovici et al., "Robotic Tools for Minimally Invasive Urologic Surgery", Dec. 2002, Internet, 1-17.

Suplee, "Mastering the Robot", The Washington Post, p. A01, Sep. 17, 2000 http://www.cs.cmu.edu-nursebot/web/press/wash/index.html.

Tendick et al., "Human-Machine Interfaces for Minimally Invasive Surgery", 1997, IEEE, pp. 2771-2776.

Thrun et al, "Probabilistic Algorithms and the Interactive Museum Tour-Guide Robot Minerva", 2000, Internet pp. 1-35.

Tzafestas, et al., "VR-based Teleoperation of a Mobile Robotic Assistant: Progress Report", 2000, Internet, pp. 1-23.

Urquhart, Kim, "InTouch's robotic Companion 'beams up' healthcare experts", Medical Device Daily, vol. 7, No. 39, Feb. 27, 2003, p. 1, 4.

Weiss et al., Telework and video-mediated communication: Importance of real-time, interactive communication for workers with disabilities, pp. 1-4, California State University Northridge, http://www.csun.edu/cod/conf/1999/proceedings/session0238.html.

West et al., "Design of Ball Wheel Mechanisms for Omnidirectional Vehicles with Full Mobility and Invariant Kinematics", Journal of Mechanical Design, vol. 119, pp. 153-161, Jun. 1997.

Yamasaki et al., Applying Personal Robots and Active Interface to Video Conference Systems, 1995, Internet, pp. 243-248.

Yong et al., "Robot task execution with telepresence using virtual reality technology", 1998, Internet, pp. 1-9.

Zamrazil, Kristie, "Telemedicine in Texas: Public Policy Concerns", House Research Organization Focus Report, Texas House of Representatives, No. 76-22, May 5, 2000 http://www.hro.house.state.tx.us/focus/telemed.pdf.

Zipperer, Lorri, "Robotic dispensing system", 1999, Internet, pp. 1-2.

Zorn, Benjamin G., "Ubiquitous Telepresence", http://www.cs.colorado.edu/~zorn/ut/vision/vision.html, Mar. 5, 1996.

Noritsugu et al., "Application of Rubber Artificial Muscle Manipulator as a Rehabilitation Robot", Mechatronics, IEEE/ASME Transactions, vol. 2, No. 4, Dec. 1997, pp. 259-267.

North, Michael, "Telemedicine: Sample Script and Specifications for a Demonstration of Simple Medical Diagnosis and Treatment Using Live Two-Way Video on a Computer Network", Greenstar Corporation, 1998, 5 pages.

Picturetel Corporation, "Introducing PictureTel Live200 for Windows NT", 1997, 63 pages.

Piquepaille, Roland, "How New Technologies are Modifying Our Way of Life", Roland Piquepaille's Technology Trends, This Blog and its RSS Feed Are Moving, Oct. 31, 2004, 2 pages.

Radvision, "Making Sense of Bandwidth the NetSense Way", Network Congestion in Unmanaged Networks Bandwidth Estimation and Adaptation Techniques, Radvision's Netsense Technology, 2010, 7 pages.

(56) References Cited

OTHER PUBLICATIONS

Reynolds et al., "Review of Robotic Telemedicine Utilization in Intensive Care Units (ICUs)", 11th Annual ATA Symposium, Tampa, Florida, 2011, 1 page.

Roach, Adam, "Automatic Call Back Service in SIP", Internet Engineering Task Force, Internet Draft, Category: Informational, Mar. 2000, 8 pages.

Roy et al., "Towards Personal Service Robots for the Elderly", Workshop on Interactive Robots and Entertainment (WIRE 2000), vol. 25, Apr. 30-May 1, 2000, 7 pages.

Tahboub et al., "Dynamics Analysis and Control of a Holonomic Vehicle With Continously Variable Transmission", Journal of Dynamic Systems, Measurement and Control ASME, vol. 124, Mar. 2002, pp. 118-126.

Telepresence Research, Inc., "Telepresence Mobile Robot System", available online at <http://www.telepresence.com/telepresence-research/TELEROBOT/>, retrieved on Nov. 23, 2010, Feb. 20, 1995, 3 pages.

Theodosiou et al., "MuLVAT: A Video Annotation Tool Based on XML-Dictionaries and Shot Clustering", 19th International Conference, Artificial Neural Networks—ICANN, Sep. 14-17, 2009, pp. 913-922.

Time, Lists, "Office Coworker Robot", Best Inventions of 2001, available online at <http://content.time.com/time/specials/packages/article/0,28804,1936165_1936255_1936640,00.html>, Nov. 19, 2001, 2 pages.

Tipsuwan et al., "Gain Adaptation of Networked Mobile Robot to Compensate QoS Deterioration", vol. 4, 28th Annual Conference of the Industrial Electronics Society, Nov. 5-8, 2002, pp. 3146-3151.

Tsui et al., "Exploring Use Cases for Telepresence Robots", 6th ACM/IEEE International Conference on Human-Robot Interaction (HRI), Mar. 2011, 7 pages.

Tyrrell et al., "Teleconsultation in Psychology: The Use of Videolinks for Interviewing and Assessing Elderly Patients", British Geriatrics Society, Age and Ageing, vol. 30, No. 3, May 2001, pp. 191-195.

Umass Lowell Robotics Lab, "Robotics Lab @ UMASS Lowell", Department of Computer Science, Brochure, 2011, 2 pages.

Weaver et al., "Monitoring and Controling Using the Internet and Java", Proceedings of the 25th Annual Conference of the IEEE Industrial Electronics Society, vol. 3, 1999, pp. 1152-1158.

Weiss, et al., "PEBBLES: A Personal Technology for Meeting Education, Social and Emotional Needs of Hospitalised Children", Personal and Ubiquitous Computing, vol. 5, No. 3, Aug. 2001, pp. 157-168.

West et al., "Design of Ball Wheel Mechanisms for Omnidirectional Vehicles with Full Mobility and Invariant Kinematics", Journal of Mechanical Design, ASME, vol. 119, Jun. 1997, pp. 153-161.

Yamauchi, Brian, "PackBot: A Versatile Platform for Military Robotics", Proceedings of SPIE for Military Robotics, 2004, pp. 228-237.

Zambroski, James, "CMU, Pitt Developing 'Nursebot'", available online at <http://www.cs.cmu.edu/~nursebot/web/press/tribunereview.html>, retrieved on Jun. 26, 2012, Oct. 27, 2000, 3 pages.

U.S. Appl. No. 10/783,760, Feb. 20, 2004, 48 pages.

International Preliminary Report on Patentability and Written Opinion Received for International Patent Application No. PCT/US2006/037076, Apr. 1, 2008, 6 pages.

International Search Report and Written Opinion Received for International Application No. PCT/US2006/037076, May 11, 2007, 6 pages.

International Preliminary Report on Patentability and Written Opinion Received for International Patent Application No. PCT/US/2007/14099, Dec. 16, 2008, 5 pages.

International Search Report Received for international Patent Application No. PCT/US2007/14099, Jul. 30, 2008, 1 page.

International Search Report Received for International Patent Application No. PCT/US2005/037347, Apr. 17, 2006, 2 pages.

International Preliminary Report on Patentability and Written Opinion Received for International Patent Application No. PCT/US2005/037347, Apr. 17, 2006, 7 pages.

Appeal from the U.S. District Court for the Central District of California in case No. 11-cv-9185, Judge Percy Anderson, Joint Appendix, vol. I of IV, Jun. 24, 2013, pp. A1-A6357.

Appeal from the U.S. District Court for the Central District of California in case No. 11-cv-9185, Judge Percy Anderson, Joint Appendix, vol. II of IV, Jun. 24, 2013, pp. A6849-A10634.

Appeal from the U.S. District Court for the Central District of California in case No. 11-cv-9185, Judge Percy Anderson, Joint Appendix, vol. III of IV, Jun. 24, 2013, pp. A10654-A15517.

Appeal from the U.S. District Court for the Central District of California in case No. 11-cv-9185, Judge Percy Anderson, Joint Appendix, vol. IV of IV, Jun. 24, 2013, pp. A15677-A18127.

Reply Brief for Defendant-Appellee VGO Communications, Inc., Appeal from the U.S. District Court for the Central District of California, in Case No. 2:11-cv-9185, Judge Percy Anderson, May 28, 2013, 75 pages.

Civil Minutes—General: Case No. CV 11-9185PA (AJWx), *InTouch Tech., Inc.* v. *VGo Commons, Inc.*, U.S. District Court for the Central District of California, Judge Percy Anderson, Sep. 10, 2012, 7 pages.

Defendant VGo Communications, Inc.'s Invalidity Contentions Pursuant to the Feb. 27, 2012 Civil Minute Order, U.S. District Court for the Central District of California, in Case No. CV11-9185 PA, May 2, 2012, 143 pages.

Defendant-Counterclaimant VGo Communications, Inc.'s Supplemental Invalidity Contentions Pursuant to the Feb. 27, 2012 Civil Minute Order, U.S. District Court for the Central District of California, Case No. CV11-9185 PA, May 14, 2012, 228 pages.

"Magne Charge", Smart Power for Electric Vehicles, General Motors Corporation, Serial No. 75189637, Registration No. 2114006, Filing Date: Oct. 29, 1996, Aug. 26, 1997, 2 pages.

Opening Brief for Plaintiff-Appellant InTouch Technologies, Inc., Appeal from the U.S. District Court for the Central District of California in Case No. 11-cv-9185, Judge Percy Anderson, Apr. 12, 2013, 187 pages.

"PictureTel Adds New Features and Functionality to its Award-Winning Live200 Desktop Videoconferencing System", PR Newswire Association, LLC, Gale, Cengage Learning, Jun. 13, 1997, 4 pages.

Reply Brief for Plaintiff-Appellant InTouch Technologies, Inc., Appeal from the U.S. District Court for the Central District of California in Case No. 11-cv-9185, Judge Percy Anderson, Jun. 14, 2013, 39 pages.

"Using your Infrared Cell Phone Camera", available online on <http://www.catsdomain.com/xray/about.htm>, retrieved on Jan. 23, 2014, Courtesy of Internet Wayback Machine, Jan. 30, 2010, 4 pages.

Office Action received for Chinese Patent Application No. 200680044698.0 on Nov. 4, 2010. (9 pages of Official Copy and 17 pages of English Translation).

Wang et al., "A Healthcare Tele-robotic System with a Master Remote Station with an Arbitrator", U.S. Appl. No. 60/449,762, filed Feb. 24, 2003, 28 pages.

Active Media, Inc., "Saphira Software Manual", Real World, Saphira Version 5.3, 1997, 105 pages.

Activmedia Robotics LLC, "Pioneer 2/PeopleBot™", Operations Manual, Version 9, Oct. 2001, 78 pages.

Adams, Chris, "Simulation of Adaptive Behavior (SAB'02)—From Animals to Animats 7", Mobile Robotics Research Group, The Seventh International Conference, available online at: <http://www.dai.ed.ac.uk/groups/mrg/MRG.html>, retrieved on Jan. 22, 2014, Aug. 4-11, 2002, 1 page.

Apple Inc., "I Phone", iPhone Series, XP002696350, Sep. 21, 2012, pp. 1-29.

Barrett, Rick, "Video Conferencing Business Soars as Companies Cut Travel; Some Travel Cuts are Permanent", available online at <http://www.ivci.com/international_videoconferencing_news_videoconferencing_news_19.html>, May 13, 2002, 2 pages.

Blaer et al., "TopBot: Automated Network Topology Detection With a Mobile Robot", IEEE, Proceedings of the 2003 International Conference on Robotics and Automation, Taipei, Taiwan, Sep. 14-19, 2003, pp. 1582-1587.

Bradner, S., "The Internet Standards Process—Revision 3", Network Working Group, Request for Comments: 2026, BCP: 9, Obsoletes: 1602, Category: Best Current Practice, Oct. 1996, pp. 1-36.

(56) References Cited

OTHER PUBLICATIONS

Brooks, Rodney A., "A Robust Layered Control System for a Mobile Robot", IEEE, Journal of Robotics and Automation, vol. 2, No. 1, Mar. 1986, pp. 14-23.

Brooks, Rodney Allen, "Flesh and Machines: How Robots Will Change Us", available online at <http://dl.acm.org/citation.cfm?id=560264&preflayout=flat%25202%2520of>, retrieved on Nov. 23, 2010, Feb. 2002, 3 pages.

Christensen et al., "BeeSoft User's Guide and Reference", Robots for the Real World™, Real World Interface, Inc ., Sep. 26, 1997, 203 pages.

Chu et al., "Detection of Target Mobile Signal Strength", Technical Development, Motorola Inc., Jan. 1999, pp. 205-206.

Dario et al., "A Robot Workstation for Diagnosis and Physical Therapy", IEEE Catalog No. 88TH0234-5, Centro "E. Piaggio" University of Pisa, Italy, 1989, pp. 67-72.

Davis, Erik, "Telefriend, Meet iRobot, The Smartest Webcam on Wheels", Wired Magazine, Issue 8.09, available online at <http://www.wired.com/wired/archive/8.09/irobot.html?pg=1&topic=&topic_set=>, retrieved on Jul. 7, 2012, Sep. 2000, 3 pages.

Dean et al., "1992 AAAI Robot Exhibition and Competition", Articles, AI Magazine, vol. 14, No. 1, 1993, 15 pages.

Dudenhoeffer et al., "Command and Control Architectures for Autonomous Micro-Robotic Forces", FY00 Project Report, Idaho National Engineering and Environmental Laboratory, Human Systems Engineering and Sciences Department, Idaho Falls, Apr. 2001, 43 pages.

Elhajj et al., "Real-Time Haptic Feedback in Internet-Based Telerobotic Operation", IEEE International Conference on Electro/Information Technology, Jun. 2000, 10 pages.

Evans et al., "HelpMate: The Trackless Robotic Courier", PYXIS, available online at <http://www.pyxis.com/>, 3 pages.

Fiorini et al., "Health Care Robotics: A Progress Report", IEEE International Conference on Robotics and Automation, vol. 2, Apr. 20-25, 1997, pp. 1271-1276.

Fong, Terrence, "Collaborative Control: A Robot-Centric Model for Vehicle Teleoperation", The Robotics Institute Carnegie Mellon University, Nov. 2001, 197 pages.

Gaidioz et al., "Synchronizing Network Probes to Avoid Measurement Intrusiveness with the Network Weather Service", High-Performance Distributed Computing, Proceedings of the Ninth International Symposium, 2000, pp. 147-154.

Garner et al., "The Application of Telepresence in Medicine", BT Technology Journal, vol. 15, No. 4, Oct. 1, 1997, pp. 181-187.

ITU, "Call Completion Supplementary Services for H.323", ITU-T, Telecommunication Standardization Sector of ITU, H.450.9, Series H: Audiovisual and Multimedia Systems, Nov. 2000, 63 pages.

ITU, "Call Intrusion Supplementary Service for H.323", ITU-T, Telecommunication Standardization Sector of ITU, H.450.11, Series H: Audiovisual and Multimedia Systems, Mar. 2001, 59 pages.

ITU, "A Far End Camera Control Protocol for Videoconferences Using H.224", Transmission of Non-Telephone Signals, ITU-T, Telecommunication Standardization Sector of ITU, H.281, Nov. 1994, 12 pages.

Jacobs et al., "Applying Telemedicine to Outpatient Physical Therapy", AMIA, Annual Symposium Proceedings, 2002, 1 page.

Knight et al., "Active Visual Alignment of a Mobile Stereo Camera Platform", Robotics and Automation, Proceedings of ICRA '00, IEEE International Conference, vol. 4, Apr. 24-28, 2000, pp. 3203-3208.

Kurlowicz et al., "The Mini Mental State Examination (MMSE)", The Hartford Institute for Geriatric Nursing, Journal of Psychiatric Research, No. 3, Jan. 1999, 2 pages.

Leifer et al., "VIPRR: A Virtually in Person Rehabilitation Robot", Proceedings of 1997 International Conference on Rehabilitation Robotics, Apr. 14-15, 1997, 4 pages.

Lemaire, Edward, "Using Communication Technology to Enhance Rehabilitation Services", Terry Fox Mobile Clinic, The Rehabilitation Centre, Ottawa, Canada, Version 2.0, 1998-2001, 104 pages.

Metz, Cade, "HP Labs", available online at <http://www.pcmag.com/article2/0,2817,1130820,00.asp>, Jul. 1, 2003, 4 pages.

Microsoft Corporation, Inc., "Microsoft NetMeeting 3 Features", available online at <http://technet.microsoft.com/en-us/library/cc723477.aspx>, retrieved on Jun. 26, 2012, 6 pages.

Minsky, Marvin, "Telepresence", OMNI Magazine, Jun. 1980, 6 pages.

Nakazato et al., "Group-Based Interface for Content-Based Image Retrieval", Proceedings of the Working Conference on Advanced Visual Interfaces, 2002, pp. 187-194.

Nakazato et al., "Group-Oriented User Interface for Digital Image Management", Journal of Visual Languages and Computing, vol. 14, No. 4, Aug. 2003, pp. 45-46.

\* cited by examiner

FIG. 10

ADVANCED CONTROLS

| Start | Patient Info (272) | NIHSS (274) | t-PA (276) | Summary |

Last Name: KANE    First Name: JESSAMINE
MRN: 3012296873    Age: 75
Gender: FEMALE     Weight: 50.50 Kgs
Patient History:   Heart Rate: 90
  Diabetes ☐

3:00:00
HR    90
BP   120/80
NHSS   3
View Images

270 — (panel)
278 — (First Name/Age/Weight/Heart Rate group)

FIG. 11

ADVANCED CONTROLS

| Start | Patient Info | NIHSS (274) | t-PA | Summary |

MIH Stroke Scale:
Level of Consciousness: Please Select: ▼
MOC Questions:
  Please Select:
  0 = Alert
  1 = Not alert
  2 = Not responsive
LOC Commands:
Best Gaze: Please Select: ▼

3:00:00
HR    84
BP   130/90
NHSS
View Images

280 — (panel)
282 — (dropdown)

FIG. 12

ADVANCED CONTROLS

| Start | Patient Info | NIHSS | t-PA (276) | Summary (294) |

Patient Weight: 77.7 Kgs    Total Dose: __ Mg
Dosage Options:              Bolus Dose: __ Mg
  0.9 mg/kg ●                (administered iVP over 1 minute)
  0.6 mg/kg ○                Infusion Date: __ Mg
Calculate                    (to infuse over 60 minutes)
Print Oder 3:00:00
HR    84
BP   130/90
NHSS
View Images 290 — (panel)
292, 296, 298, 300, 302 (callouts)

FIG. 13

DOCUMENTATION THROUGH A REMOTE PRESENCE ROBOT

BACKGROUND OF THE INVENTION

1. Field of the Invention

The subject matter disclosed generally relates to a robotic tele-presence system.

2. Background Information

Robots have been used in a variety of applications ranging from remote control of hazardous material to assisting in the performance of surgery. For example, U.S. Pat. No. 5,762, 458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

There has been marketed a mobile robot introduced by InTouch-Health, Inc., the assignee of this application, under the trademark RP-7. The InTouch robot is controlled by a user at a remote station. The remote station includes personal computer with a joystick that allows the user to remotely control the movement of the robot. Both the robot and remote station have cameras, monitors, speakers and microphones to allow for two-way video/audio communication.

The InTouch RP-7 system is used by medical personnel to remotely "visit" a patient. The system is particularly useful for medical specialist. For example, medical personnel specializing in patient stroke care can remotely examine, diagnose and prescribe a patient management plan. With the proliferation of such robots it would be desirable to track and store data related to tele-presence sessions.

BRIEF SUMMARY OF THE INVENTION

A robotic system with a robot that has a camera and a remote station coupled to the robot. The remote station controls the robot in a session that results in session content data. The system further includes a storage device that stores the session content data.

BRIEF DESCRIPTION OF THE DRAWINGS

FIG. 10 is a graphical user interface at the remote station;

FIG. 11 is a graphical user interface when a NIHSS tab is selected;

FIG. 12 is a graphical user interface displayed when a t-PA table is selected

FIG. 13 is a graphical user interface displayed when a view images button is selected.

DETAILED DESCRIPTION

Disclosed is a robotic system that is used in a tele-presence session. For example, the system can be used by medical personnel to examine, diagnose and prescribe medical treatment in the session. The system includes a robot that has a camera and is controlled by a remote station. The system further includes a storage device that stores session content data regarding the session. The data may include a video/audio taping of the session by the robot. The session content data may also include time stamps that allow a user to determine the times that events occurred during the session. The session data may be stored on a server that is accessible to multiple users. Billing information may be automatically generated using the session data.

Figure 1:
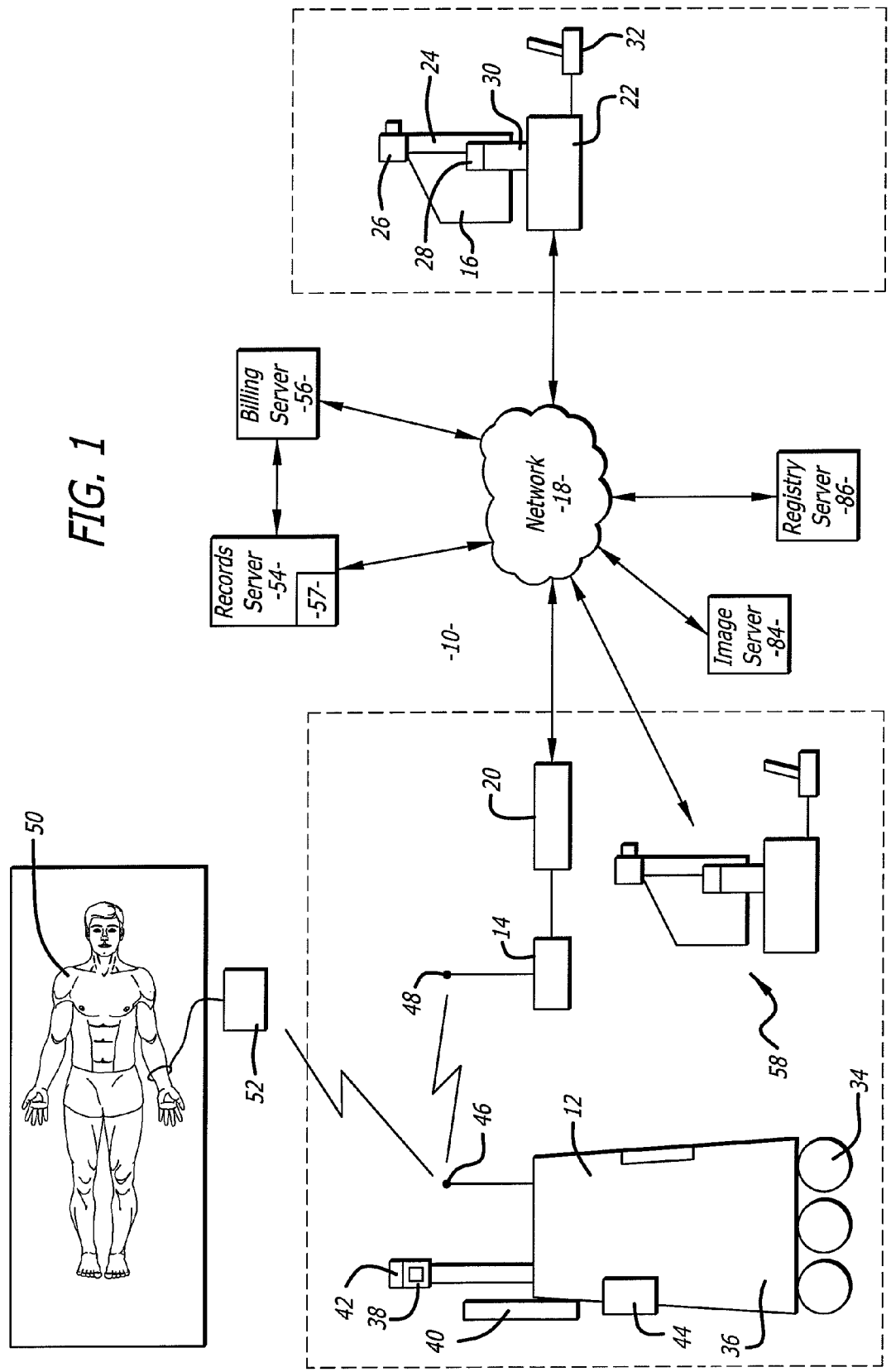
FIG. 1 is an illustration of a robotic system.

Referring to the drawings more particularly by reference numbers, FIG. 1 shows a robotic system 10. The robotic system 10 includes one or more robots 12. Each robot 12 may have a base station 14. The robot 12 is coupled to a remote control station 16. The remote control station 16 may be coupled to the base station 14 through a network 18. By way of example, the network 18 may be either a packet switched network such as the Internet, or a circuit switched network such has a Public Switched Telephone Network (PSTN) or other broadband system. The base station 14 may be coupled to the network 18 by a modem 20 or other broadband network interface device. By way of example, the base station 14 may be a wireless router. Alternatively, the robot 12 may have a direct connection to the network 18 through, for example, a satellite.

The remote control station 16 may include a computer 22 that has a monitor 24, a camera 26, a microphone 28 and a speaker 30. The computer 22 may also contain an input device 32 such as a joystick or a mouse. The control station 16 is typically located in a place that is remote from the robot 12. Although only one remote control station 16 is shown, the system 10 may include a plurality of remote stations. In general any number of robots 12 may be controlled by any number of remote stations 16 or other robots 12. For example, one remote station 16 may be coupled to a plurality of robots 12, or one robot 12 may be coupled to a plurality of remote stations 16, or a plurality of robots 12.

Each robot 12 includes a movement platform 34 that is attached to a robot housing 36. The robot 12 may also have a camera 38, a monitor 40, a microphone(s) 42 and a speaker(s) 44. The microphone 42 and speaker 30 may create a stereophonic sound. The robot 12 may also have an antenna 46 that is wirelessly coupled to an antenna 48 of the base station 14. The system 10 allows a user at the remote control station 16 to move the robot 12 through operation of the input device 32. The robot camera 38 is coupled to the remote monitor 24 so that a user at the remote station 16 can view someone at the robot site such as a patient. Likewise, the robot monitor 40 is coupled to the remote camera 26 so that someone at the robot site can view the user. The microphones 28 and 42, and speakers 30 and 44, allow for audible communication between the robot site and the user of the system.

The remote station computer 22 may operate Microsoft OS software and WINDOWS XP or other operating systems such as LINUX. The remote computer 22 may also operate a video driver, a camera driver, an audio driver and a joystick driver. The video images may be transmitted and received with compression software such as MPEG CODEC.

The system 10 can be used to engage in a session that results in data. For example, the system 10 can be used by medical personnel to remotely examine, diagnose and prescribe a patient management plan for a patient 50 in a medical session. Either the patient, or a bed supporting the patient, may have a radio frequency information device ("RFID") 52. The RFID 52 may wirelessly transmit information that is received by the robot 12 through antennae 46. The RFID information can be used to correlate a particular session with a specific patient. The receipt of RFID information may initiate the storage of session data. Although a medical session is described, it is to be understood that other types of sessions may be conducted with the system 10. For example, the system 10 may be used to move the robot(s) about a factory floor wherein the user provides remote consultation. Consultation session data may be stored by the system 10.

The system can store and display session content data. Session content data is information regarding the substance of a session. For example, in a medical application, session content data would include physician notes, diagnosis and prescription information. In a factory-equipment repair application, session content data would include repair methodology and replaced parts. Session content data would not be mere time entries associated with the logging on and termination of a robot session.

The system 10 may include a records server 54 and/or a billing server 56 that can be accessed through the network 18. The servers 54 and 56 may include memory, processors, I/O interfaces and storage devices such as hard disk drives, as is known in the art. Records server 54 may have a storage device(s) 57 that stores session data. The server 54 may receive and store session data during a session. For example, the server 54 may receive and store video and audio captured by the robot camera 38 and microphone 42, respectively. To reduce bandwidth requirements during a session the session data, such as video/audio segments, can be transmitted from the robot 12 to the server 54 after the session has terminated. For example, when the user logs off the system. Timestamped progress notes are also simultaneously uploaded. The server 54 may contain other medical records of a patient such as written records of treatment, patient history, medication information, laboratory results, physician notes, etc. Video/audio segments can be timestamped and associated with the identification of the control station and the robot, and a unique identifier which can be cross-referenced with progress notes and other session data. These video/audio segments can then later be used to substantiate and reference the various progress notes and other events in a visual fashion. The system can track all head and base movements made during the course of the associated portion of the session, to allow correlation of those movements with the actions taken.

The system 10 may include a user interface 58 that allows a user at the remote location to enter data into the system. For example, the interface 58 may be a computer or a computer terminal that allows a user to enter information about the patient. The robot 12 can be moved into view of the patient through the remote station 16 so that patient information can be entered into the system while a physician is viewing the patient through the robot camera. The physician can remotely move the robot 12 to obtain different viewing angles of the patient. The user interface 58 may be a separate computer and/or be integral with the robot 12. The billing server 56 may automatically generate a bill from the information provided by the session data on a periodic basis. The billed elements may be based on either actions performed or outcomes achieved, or both. Alternatively, a user can manually generate bills through a user interface to the billing server.

The billing server 56 may receive session data during a session or upon termination of a session. Additionally, the billing server may poll a robot to retrieve data from its hard drive. The session data may be organized so as to automatically populate certain fields of a billing statement or report. The billing information can be automatically sent to an insurance carrier.

Figure 2:
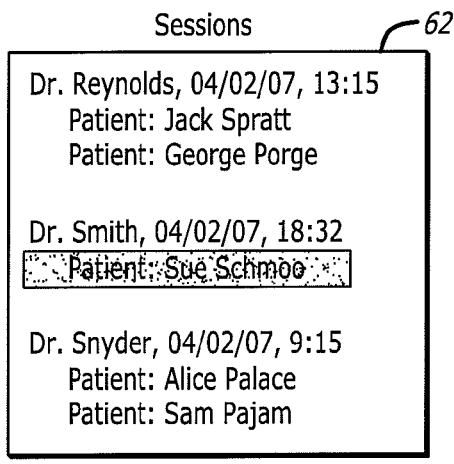
FIG. 2 is an illustration showing a user interface.
Figure 3:
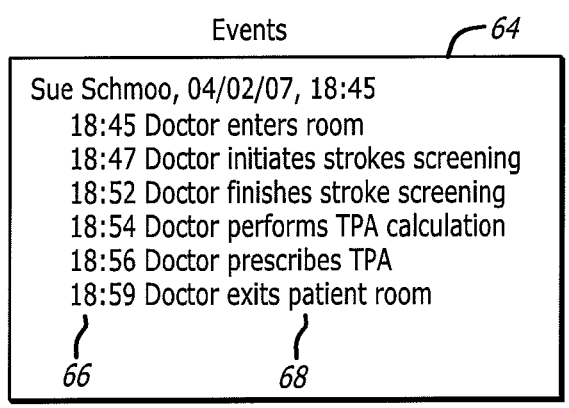
FIG. 3 is an illustration of a user interface displaying events and associated time stamps.

The server 54 can be accessible through a web page or other means for accessing information through a network 18. FIG. 2 shows a user interface 62 displayed at a remote station 16, or any other terminal that can access the server 54. The interface 62 can for example, provide a date and time that various physicians had sessions with different patients. FIG. 3 shows another user interface 64 that displays time stamps 66 that are associated with certain events 68. Records can be retrieved by various filters including physician name, patient name, time of session and services performed during the session. The event data can be initially stored in either the robot 12 or the remote station 16 and then loaded into the server 54, either during or after a session. Alternatively, event data can be directly loaded into the server without storing it locally on the robot or remote station.

Figure 4:
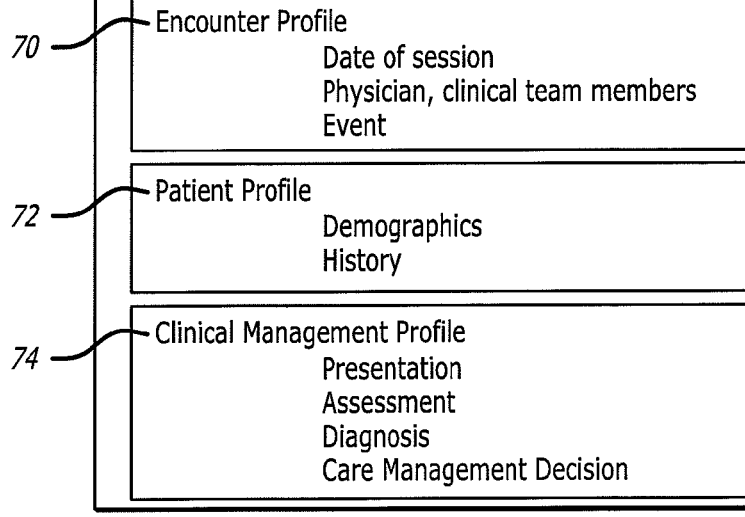
FIG. 4 is an illustration of a user interface with selectable fields.
Figure 5:
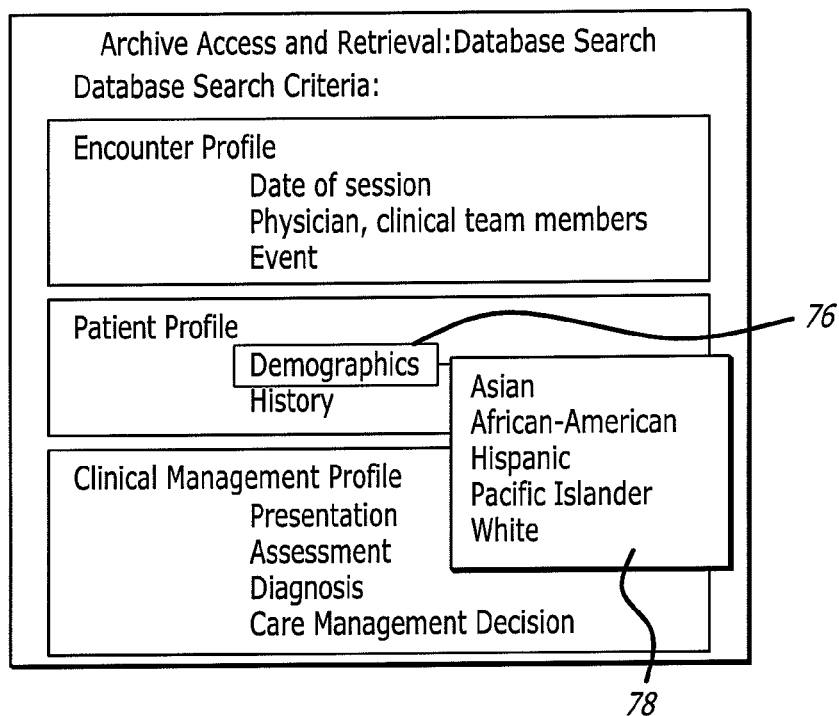
FIG. 5 is an illustration showing the display of a pull-down menu.
Figure 6:
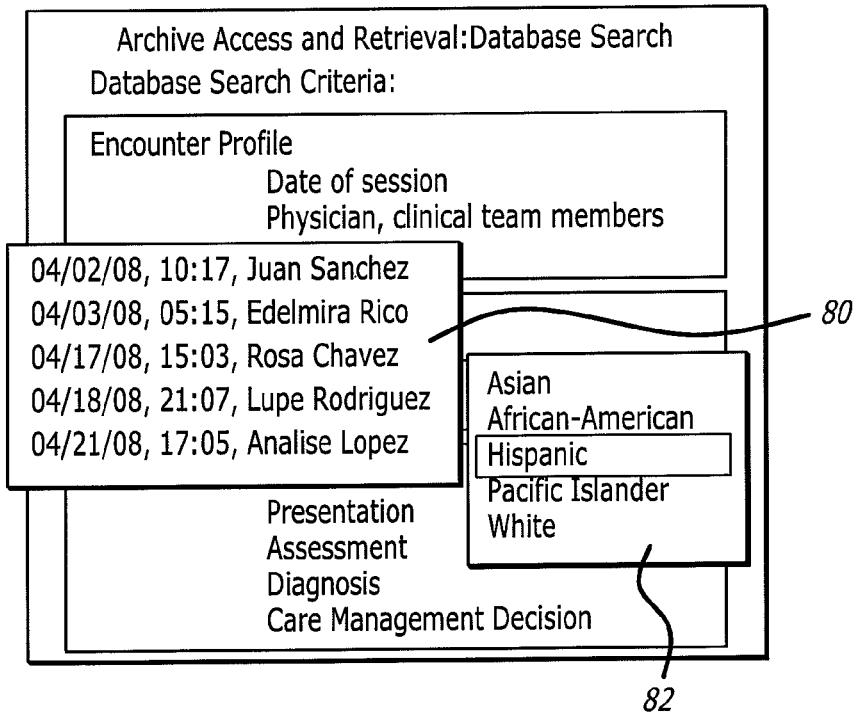
FIG. 6 is an illustration showing a session field displayed in response to the selection of a field.

The session data can be organized into a plurality of data types. FIG. 4 shows a plurality of different data types. For example, the session data can be organized into ENCOUNTER PROFILE data 70, PATIENT PROFILE data 72 and CLINICAL MANAGEMENT PROFILE data 74, with each having subfields such as EVENT and HISTORY. FIG. 5 shows a pull-down screen 78 that is displayed when a DEMOGRAPHICS field 76 is selected. FIG. 6 shows a field 80 that displays a number of sessions that match a selected HISPANIC field 82. The session data can be searched with Boolean operators such as AND and OR to search for multiple terms, data types, etc. The user can display all hits for the search, or have a statistical analysis performed based on the matching sessions.

In a factory equipment-repair application, the equipment being repaired during the session would replace the patient name in FIG. 2; and steps for repair would replace the event list in FIG. 3. Repair methodologies and affected part numbers would replace the search criteria in FIGS. 4, 5 and 6. Captured video and audio would show the steps in the repair process, and would be timestamped and cross-referenced to the data in FIG. 3.

Referring to FIG. 1, the system 10 may also include an image server 84 and a registry server 86. The image server 84 may include medical images. For example, the medical images may include CT scans of a patient's brain. The images can be downloaded to one of the remote stations 16 through the network 18. The registry server 86 may store historical data on patients. The historical data can be downloaded to a remote computer 16 through the network 18.

Figure 7:
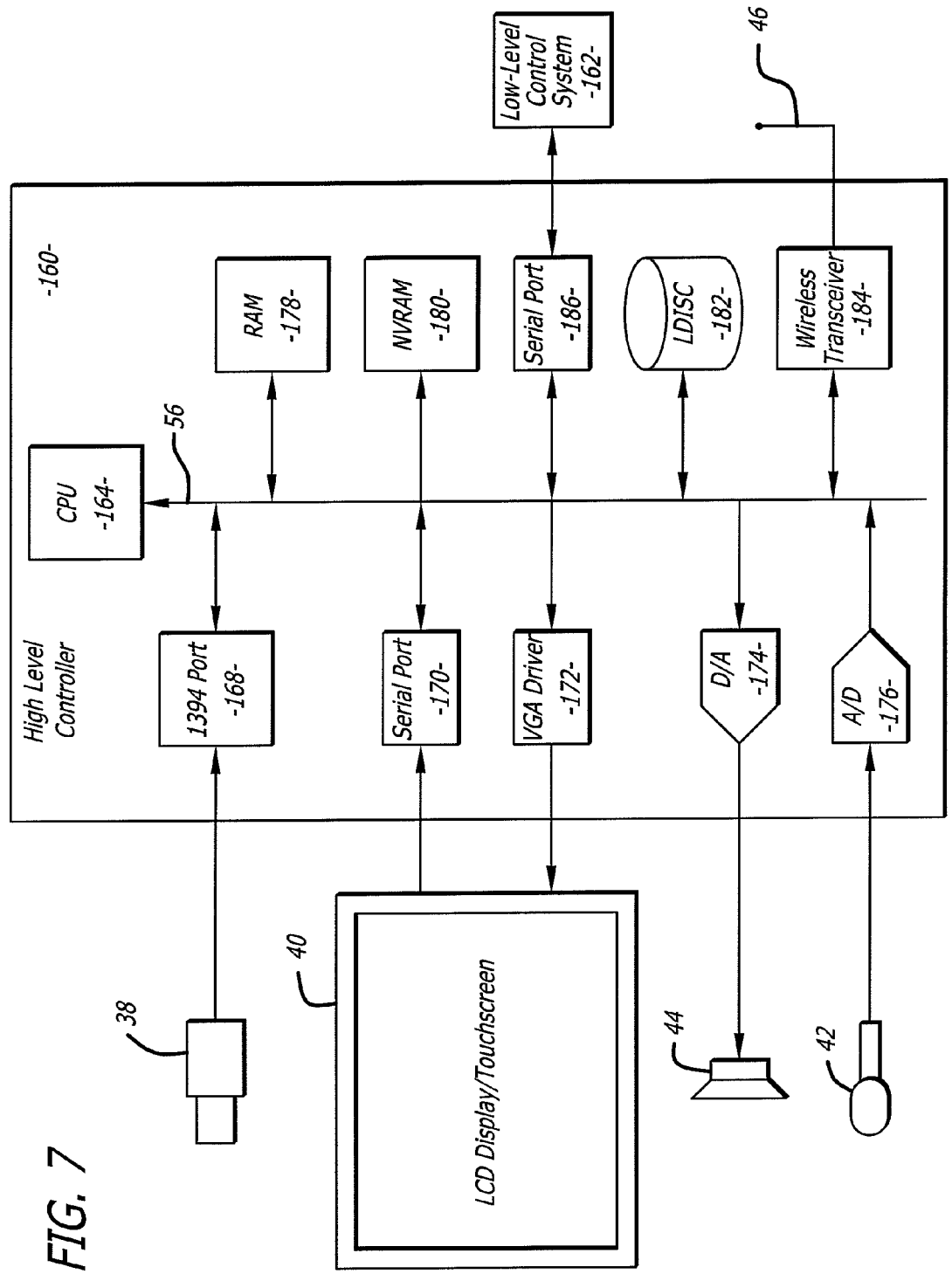
FIG. 7 is a schematic of an electrical system of a robot.

FIG. 7 shows an embodiment of a robot 12. Each robot 12 may include a high level control system 160 and a low level control system 162. The high level control system 160 may include a processor 164 that is connected to a bus 166. The bus is coupled to the camera 38 by an input/output (I/O) port 168, and to the monitor 40 by a serial output port 170 and a VGA driver 172. The monitor 40 may include a touchscreen function that allows a user to enter input by touching the monitor screen.

The speaker 44 is coupled to the bus 166 by a digital to analog converter 174. The microphone 42 is coupled to the bus 166 by an analog to digital converter 176. The high level controller 160 may also contain random access memory (RAM) device 178, a non-volatile RAM device 180 and a mass storage device 182 that are all coupled to the bus 172. The RAM 178, NVRAM 180 and/or mass storage device 182 may contain session data that is transmitted to the remote station and/or server. The robot antennae 46 may be coupled to a wireless transceiver 184. By way of example, the transceiver 184 may transmit and receive information in accordance with IEEE 802.11b.

The controller 164 may operate with a LINUX OS operating system. The controller 164 may also operate MS WINDOWS along with video, camera and audio drivers for communication with the remote control station 16. Video information may be transceived using MPEG CODEC compression techniques. The software may allow the user to send e-mail to the patient and vice versa, or allow the patient to access the Internet. In general the high level controller 160 operates to control communication between the robot 12 and the remote control station 16.

The high level controller 160 may be linked to the low level control system 162 by a serial port 186. The low level control system 162 may include components and software that mechanically actuate the robot 12. For example, the low level control system 162 provides instructions to actuate the movement platform to move the robot 12. The low level control system 162 may receive movement instructions from the high level controller 160. The movement instructions may be received as movement commands from the remote control station or another robot. Although two controllers are shown, it is to be understood that each robot 12 may have one controller, or more than two controllers, controlling the high and low level functions.

The system may be the same or similar to a robotic system provided by the assignee InTouch Technology, Inc. of Santa Barbara, Calif. under the name RP-7, which is hereby incorporated by reference. The system may also be the same or similar to the system disclosed in U.S. Pat. No. 7,292,912, which is hereby incorporated by reference.

Figure 8:
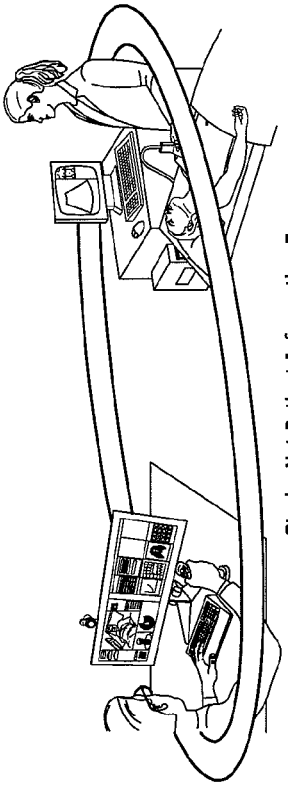
FIG. 8 is a graphical user interface of a user interface.

FIG. 8 shows a graphical user interface 250 can be provided at the user interface 58. The graphical user interface 250 includes a plurality of data fields 252 that can be filled by the user. The data fields 252 can request patient information such as name, age, etc. The data fields may also include request for medical data such as heart rate, glucose level and blood pressure ("SBP" and "DBP"). The data entered into the fields 252 can be included in the session data that is transmitted and stored by the system 10. Filling the data fields may be designated an "event" that is given as associated time stamp and displayed by a user interface.

Figure 9:
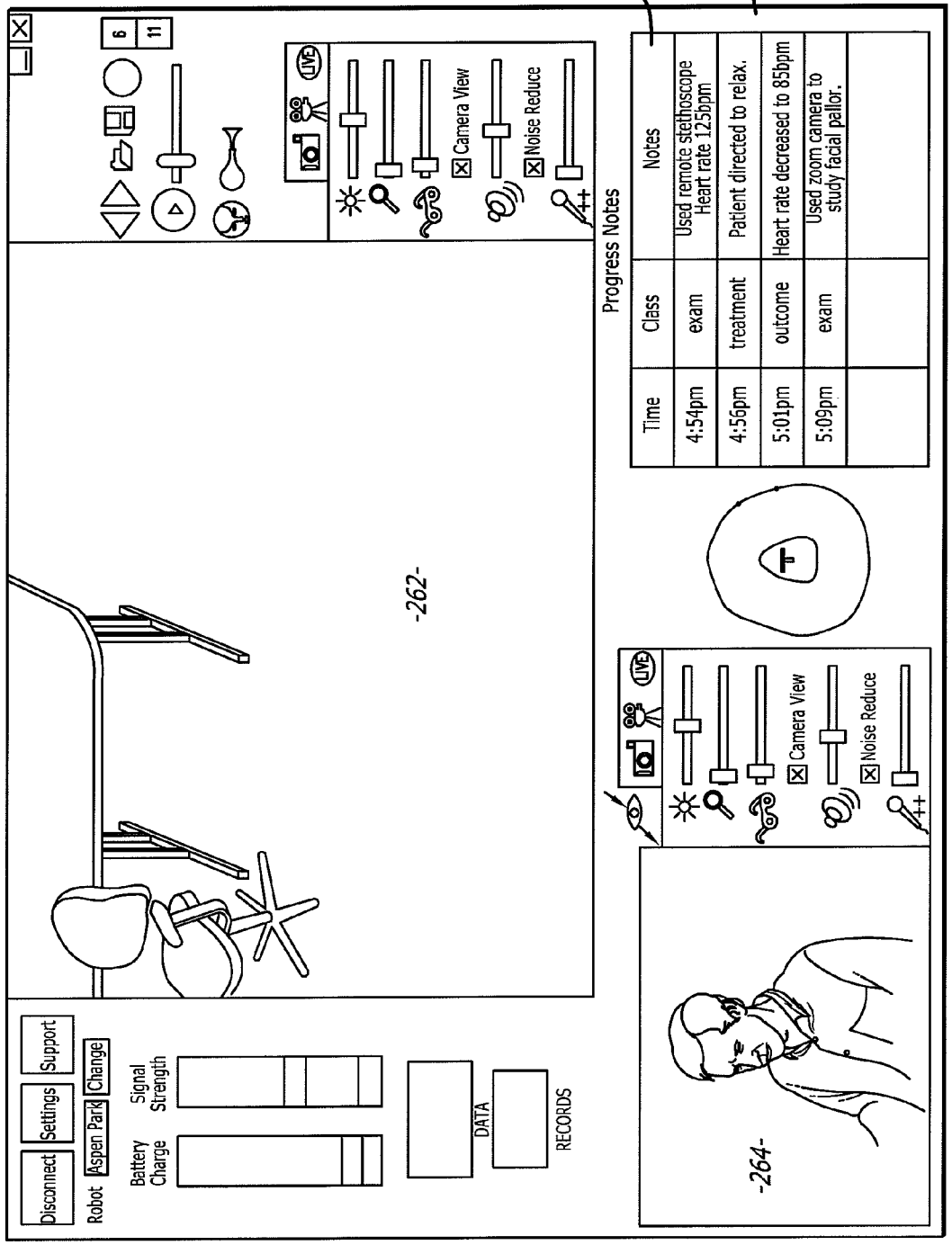
FIG. 9 is a graphical user interface at a remote station.

FIG. 9 shows a display user interface ("DUI") 260 that can be displayed at the remote station 16. The DUI 260 may include a robot view field 262 that displays a video image captured by the camera of the robot. The DUI 260 may also include a station view field 264 that displays a video image provided by the camera of the remote station 16. The DUI 260 may be part of an application program stored and operated by the computer 22 of the remote station 16. The video and any accompanying audio displayed by the robot and station view fields may be transmitted and stored by the system 10 as session data.

The DUI 260 may contain a "progress notes" text editing field, which enables a "document as you treat" methodology. As the physician conducts treatment, he can document both the treatment steps and outcomes in the progress notes field. Each note may be manually timestamped by the physician, or automatically timestamped by the software based on when the physician began typing each note. In the application of factory floor equipment repair, the progress notes would detail the various examinations and repair steps taken.

FIG. 10 shows a graphical user interface 270 that can be displayed by the monitor of the remote station 16. The interface 270 includes a "PATIENT INFO" tab 272, a "NIHSS" tab 274 and a "t-PA" tab 276. Selection of the PATIENT INFO tab 272 displays various data fields 278 including patient name, age, weight, heart rate, etc. This may be the same information entered through the user interface 250. This information may be included in the session data that is transmitted and stored by the system 10. The usage of this interface may be tagged as an event with an associated time stamp.

FIG. 11 shows an interface 280 when the "NIHSS" tab 274 is selected. The interface 280 has a data field 282 that provides a questionnaire to rate the severity of a stroke victim using the NIHSS stroke scale. This provides a readily available medical tool for the physician. The results of the questionnaire can be included in the session data and be tagged as an event that has an associated time stamp.

Figure 13:
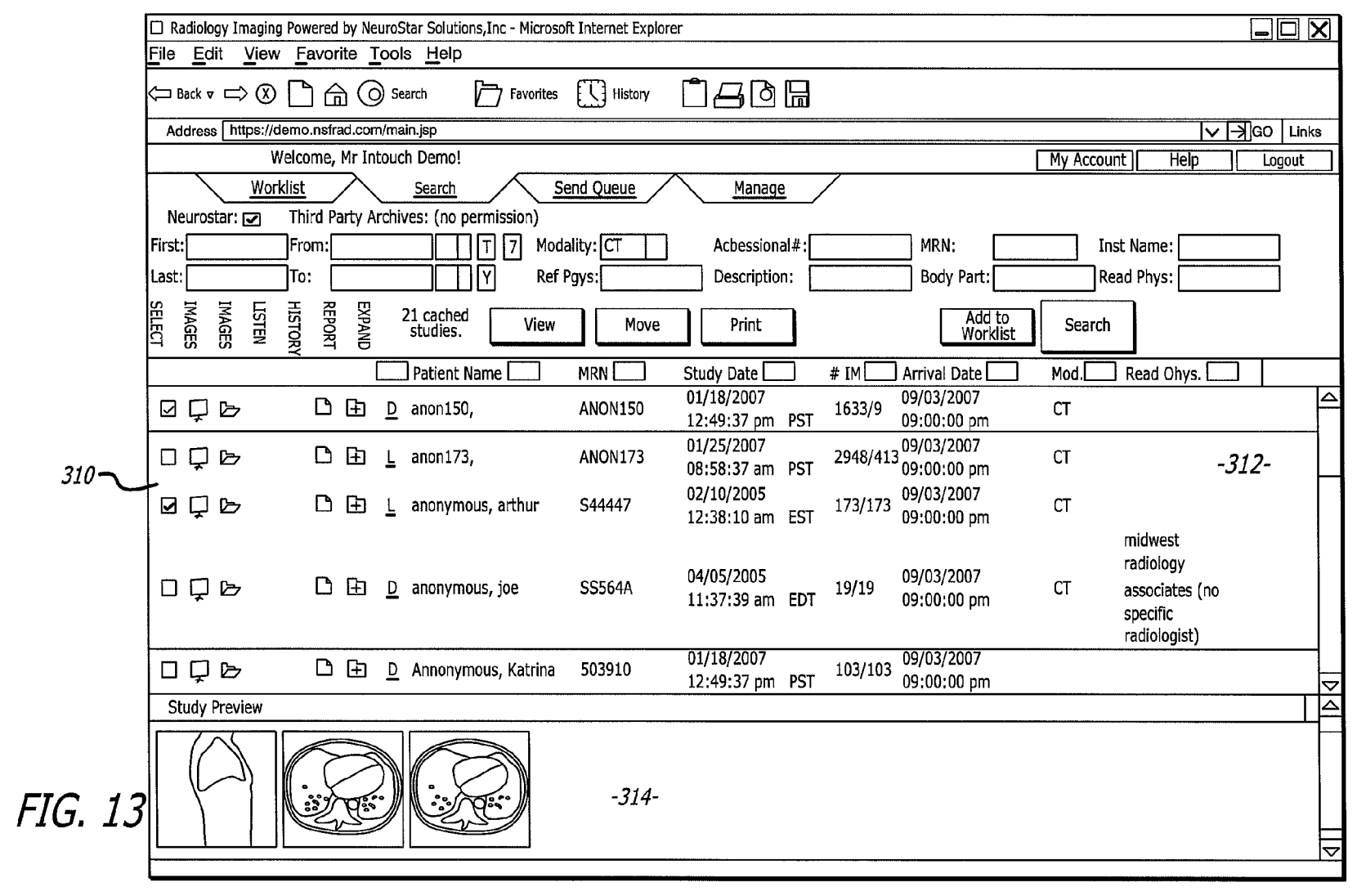

FIG. 12 shows an interface 290 when the "t-PA" tab 276 is selected. The interface 290 may include a data field 292 that provides the patient's weight, a "TOTAL DOSE" data field 294, a "BOLUS DOSE" data field 296 and an "INFUSION DOSE" data field 298. The interface 290 may also include a "CALCULATE" button 300. When the CALCULATE button 300 is selected the data fields 294, 296 and 298 are automatically populated with a calculated dosage. This provides a patient management plan for the physician to review. The interfaces 270, 280 and 290 also have a "VIEW IMAGES" button 302 that when selected displays an interface 310 shown in FIG. 13. The interface 310 includes a data field 312 and an image field 314. The image field 314 can provide a plurality of medical images such as a CT scan of the patient's head.

The calculated dosage and images can be included in the session data that is transmitted and stored by the system. The automatic population of the data fields may be tagged as an event with an associated time stamp. Likewise, the selection of the data and/or image fields may be tagged as events with time stamps.

The system is useful for allowing a physician to remotely view and treat a stroke patient. The system provides patient information, NIHSS stroke severity assessment, calculated t-PA dosage and CT head images that allow the physician to provide real time remote patient treatment. The system also allows such sessions to be audited so that medical personnel, healthcare institutions, insurance carriers, etc. can audit sessions. Such audits may include viewing video/audio captured by the robot during a session.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A robotic system, comprising:
a robot that has a robot camera, a robot monitor, a robot microphone, and a robot speaker;
a remote station that has a station camera, a station monitor, a station microphone, and a station speaker, said remote station and said robot are capable of establishing a telepresence session during which said station monitor is coupled to said robot camera and displays a robot image captured by said robot camera, said robot monitor is coupled to said station camera and displays a station image captured by said station camera, said station speaker is coupled to said robot microphone, and said robot speaker is coupled to said station microphone to enable two-way audio communication between said robot and said remote station, said remote station controls said robot during said telepresence session and said telepresence session results in session content data that is non-image and non-audio data; and, a storage device that stores said session content data during said telepresence session.

2. The system of claim 1, wherein said storage device includes a server.

3. The system of claim 1, wherein said session content data is correlated with a movement of said robot.

4. The system of claim 1, wherein said session content data is searchable.

5. The system of claim 1, wherein said session content data includes at least one time stamp.

6. The system of claim 5, wherein said remote station provides a graphical user interface that displays said time stamp and said session content data.

7. The system of claim 6, wherein said session content data is entered by an operator at said remote station.

8. The system of claim 7, wherein said time stamp is automatically generated when said session content data is entered by the operator.

9. The system of claim 1, further comprising a billing server that generates a bill with said session content data.

10. The system of claim 1, further comprising a bill that is based on an action of said session content data.

11. The system of claim 1, wherein said session content data is structured into a plurality of data types and is searchable across said data types.

12. A robotic system, comprising:
   a robot that has a camera that captures an image;
   a remote station that has a station camera, a station monitor, a station microphone, and a station speaker, said remote station and said robot are capable of establishing a telepresence session during which said station monitor is coupled to said robot camera and displays a robot image captured by said robot camera, said robot monitor is coupled to said station camera and displays a station image captured by said station camera, said station speaker is coupled to said robot microphone, and said robot speaker is coupled to said station microphone to enable two-way audio communication between said robot and said remote station, said remote station controls said robot in a session that results in session content data that is non-image and non-audio data; and,
   means for storing said session content data.

13. The system of claim 12, wherein said session content data is searchable.

14. The system of claim 12, wherein said session content data includes at least one time stamp.

15. The system of claim 14, wherein said remote station provides a graphical user interface that displays said time stamp and said session content data.

16. The system of claim 15, wherein said session content data is entered by an operator at said remote station.

17. The system of claim 16, wherein said time stamp is automatically generated when said session content data is entered by the operator.

18. The system of claim 12, further comprising a billing server that generates a bill with said session content data.

19. The system of claim 12, further comprising a bill that is based on an action of said session content data.

20. The system of claim 12, wherein said session content data is structured into a plurality of data types and is searchable across said data types.

21. A method for conducting a tele-presence session, comprising:
   moving a robot through control of a remote station, the robot has a robot camera, a robot monitor, a robot microphone and a robot speaker, the remote station includes a station camera, a station monitor, a station microphone and a station speaker;
   establishing a telepresence session during which the station monitor is coupled to the robot camera and display a robot image captured by the robot camera, said robot monitor is coupled to the station camera and displays a station image captured by the station camera, the station speaker is coupled to the robot microphone, and the robot speaker is coupled to the station microphone to enable two-way audio communication between said robot and the remote station;
   engaging in a session that results in session content data that is non-image and non-audio data; and,
   storing the session content data during the telepresence session.

22. The method of claim 21, wherein the session content data is searchable.

23. The method of claim 21, further comprising generating at least one time stamp for the session content data.

24. The method of claim 23, further comprising displaying the time stamp and the session content data.

25. The method of claim 24, wherein the session content data is entered by an operator at the remote station.

26. The method of claim 25, wherein the time stamp is automatically generated when the session content data is entered by the operator.

27. The method of claim 21, further comprising transmitting a video image of a user at the control station to a monitor of the robot.

28. The method of claim 21, further comprising automatically generating a bill with the session content data.

29. The method of claim 21, further comprising structuring the session content data into a plurality of data types and searching the session content data across the data types.

* * * * *